US006743788B2

(12) United States Patent
Cirillo et al.

(10) Patent No.: US 6,743,788 B2
(45) Date of Patent: Jun. 1, 2004

(54) CARBAMATE AND OXAMIDE COMPOUNDS

(75) Inventors: Pier Francesco Cirillo, Woodbury, CT (US); Victor Kamhi, Danbury, CT (US); John Robinson Regan, Larchmont, NY (US); Michele Tsang, Calgary (CA)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 13 days.

(21) Appl. No.: 10/147,675

(22) Filed: May 17, 2002

(65) Prior Publication Data

US 2003/0092702 A1 May 15, 2003

Related U.S. Application Data

(60) Provisional application No. 60/293,600, filed on May 25, 2001.

(51) Int. Cl.⁷ ............... C07D 413/14; C07D 413/12; A61P 19/02; A61P 17/06; A61K 31/5377
(52) U.S. Cl. ............... 514/217.05; 544/121; 544/122; 544/124; 544/128; 544/129; 544/135; 544/139; 544/143; 544/160; 544/165; 544/146; 544/153; 544/149; 544/60; 544/62; 540/598; 514/227.8; 514/231.8; 514/232.2; 514/235.5; 514/235.8; 514/236.6; 514/237.2; 514/239.5
(58) Field of Search ............... 544/121, 122, 544/128, 129, 124, 135, 137, 139, 143, 160, 165, 166, 153, 149, 62, 60; 540/598; 514/217.05, 227.8, 231.8, 232.2, 235.5, 235.8, 236.5, 236.6, 237.2, 239.5

(56) References Cited

U.S. PATENT DOCUMENTS

| 4,435,567 | A | 3/1984 | Lugosi et al. |
| 6,211,373 | B1 | 4/2001 | Widdowson et al. |
| 6,262,113 | B1 | 7/2001 | Widdowson et al. |
| 6,297,381 | B1 | 10/2001 | Cirillo et al. |
| 6,319,921 | B1 | 11/2001 | Cirillo et al. |
| 6,329,415 | B1 | 12/2001 | Cirillo et al. |
| 6,333,325 | B1 | 12/2001 | Cirillo et al. |
| 6,358,945 | B1 | 3/2002 | Cirillo et al. |

FOREIGN PATENT DOCUMENTS

| EP | 0 395 144 | 10/1990 |
| EP | 0 418 071 A2 | 3/1991 |
| WO | WO 93/24458 | 12/1993 |
| WO | WO 94/18170 | 8/1994 |
| WO | WO 97/16442 | 5/1997 |
| WO | WO 98/52558 | 11/1998 |
| WO | WO 98/52559 | 11/1998 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/32463 | 7/1999 |
| WO | WO 00/18738 | 4/2000 |
| WO | WO 00/55139 | 9/2000 |
| WO | WO 01/36403 | 5/2001 |

OTHER PUBLICATIONS

Chalmers (TiPS vol 17, pp. 166–172 Apr. 1996).*
"News & Notices" <http://www.psoriasis.org/enbrel.approval.jan.02.htm> downloaded on Jul. 30, 2002.*
"Centocor Places Congestive Heart Failure Clinical Program On Hold" <http://www.jnj.com/news/jnj_news/20020329_0810.htm> downloaded on Sep. 10, 2003.*
Stephen A. Paget, <http://rheumatology.hss.edu/phys/specialReports/pagetTNF.asp> downloaded on Mar. 07, 2002.*
"Remicade Ineffective For CHF" <http://arthritis.about-.com/library/weekly/aa102401a.htm> downloaded on Sep. 10, 2003.*
et al, Proc. Soc. Exp. Biol. and Medicine 223, 128 (2000).*
International Search Report.

* cited by examiner

Primary Examiner—Mark L. Berch
Assistant Examiner—Kahsay Habte
(74) Attorney, Agent, or Firm—Robert P. Raymond; Anthony P. Bottino; Timothy X. Witkowski

(57) ABSTRACT

Disclosed are novel aromatic compounds of the formula(I) described herein, wherein G, E, W, Ar, X, Y and Z are disclosed herein. The compounds are useful for treating cytokine mediated diseases or conditions such as chronic inflammatory diseases. Also disclosed are pharmaceutical compositions containing and processes of making such compounds.

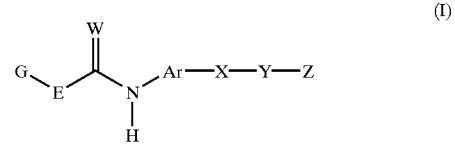

24 Claims, No Drawings

CARBAMATE AND OXAMIDE COMPOUNDS

RELATED APPLICATION DATA

This application claims benefit to U.S. provisional application No. 60/293,600 filed May 25, 2001.

TECHNICAL FIELD OF THE INVENTION

This invention relates to novel compounds which inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, Rev. Infect. Disease 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, J. Invest. Med. 43: 28–38). Studies suggest that inflammatory changes mediated by cytokines may be involved in the pathogenesis of restenosis after percutaneous transluminal coronary angioplasty (PTCA) (Tashiro, H., et al., 2001 Mar, Coron Artery Dis 12(2):107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, British J. Rheum. 35: 334–342 and Stack, W. A., et al., 1997, Lancet 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, Nature Biotechnology 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, Inflamm. Res. 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, Nutrution 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, Biomed Pharmacother. 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, J Bone Miner Res. 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, Proc Soc Exp Biol Med. 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., Proc. Natl. Acad. Sci. U.S.A, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al, 1996, Aliment Pharmacol Ther. 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-I (Holden, et al., 1995, Med Hypotheses, 45, 559). A role for IL-1 in the pathogenesis of human immunodeficiency virus (HIV) has been identified.

IL-1ra showed a clear relationship to acute inflammatory events as well as to the different disease stages in the pathophysiology of HIV infection (Kreuzer, et al., 1997, Clin Exp Immunol. 109, 54). IL-1 and TNF are both involved in periodontal disease. The destructive process associated with periodontal disease may be due to a disregulation of both IL-1 and TNF (Howells, 1995, Oral Dis. 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J Resp. & Crit.* Care Med.,161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Bodjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al, 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis. Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5:42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21:487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including bum-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *LeukLymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilboum, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophaty, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

In view of the work cited above there is a clear need for compounds that inhibit cytokine production in order to treat various disease states.

It is therefore an object of the invention to provide novel carbamate and oxamide compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In the broadest generic aspect of the invention, there is provided compounds of the formula(I):

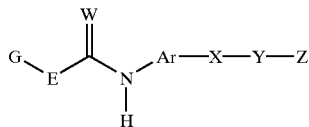

wherein:
E is
is a group chosen from —O—, —NH— and —S—;
G is:
phenyl, naphthyl, benzocyclobutanyl, dihydronaphthyl, tetrahydronaphthyl, benzocycloheptanyl, benzocycloheptenyl, indanyl, indenyl;
pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzooxazolyl, benzofuranyl, benzothiophenyl, benzpyrazolyl, dihydrobenzofuranyl, dibenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, 2,3-dihydro-1H-indolyl, indolinyl, indolonyl, indolinonyl, phthalimidyl, chromoyl;
oxetanyl, pyrrolidinyl, tetrahydrofuranyl, tetrahydrothiophenyl, piperidinyl, piperazinyl, morpholino, tetrahydropyranyl, dioxanyl, tetramethylene sulfonyl, tetramethylene sulfoxidyl, oxazolinyl, 3,4-dihydro-2H-benzo[1,4]oxazinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholino, thiazolidinyl, dihydrooxazinyl, dihydropyranyl, oxocanyl, heptacanyl, thioxanyl or dithianyl;
wherein G is substituted by one $R_3$ and further substituted by one or more $R_1$ or $R_2$;
Ar is:
phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more R4 or $R_5$;

X is:
a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;
aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;
Y is:
a bond or a $C_{1-10}$ saturated or unsaturated branched or unbranched carbon chain, wherein one or more C atoms are optionally replaced by O, N, or $S(O)_m$; and wherein Y is optionally partially or fully halogenated and optionally independently substituted with one to two oxo groups, nitrile, amino, imino, phenyl or one or more $C_{1-4}$ alkyl optionally substituted by one or more halogen atoms;
Z is:
aryl, heteroaryl selected from pyridinyl, piperazinyl, pyrimidinyl, pyridazinyl, pyrazinyl, imidazolyl, pyrazolyl, triazolyl, tetrazolyl, furanyl, thienyl and pyranyl, heterocycle selected from tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino;
or Z is optionally substituted with one to three amino or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;
or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;
or Z is hydroxy, halogen, nitrile, amino wherein the N atom is optionally independently mono- or di-substituted by $C_{1-3}$acyl, $C_{1-6}$alkyl or $C_{1-3}$alkoxy$C_{1-3}$alkyl, $C_{1-6}$alkyl branched or unbranched, $C_{1-6}$alkoxy, $C_{1-3}$acylamino, nitrile$C_{1-4}$alkyl, $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;
each $R_1$ is independently:

$C_{1-10}$ alkyl branched or unbranched optionally partially or fully halogenated, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl, or $R_1$ is cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, nitrile, hydroxy$C_{1-3}$alkyl or aryl;

phenyloxy or benzyloxy each being optionally partially or fully halogenated and optionally substituted with one to three $C_{1-3}$ alkyl groups optionally partially or fully halogenated, nitrile, hydroxy$C_{1-3}$alkyl or aryl;

cyclopropyl, cyclobutyl, cyclopentyl, cyclohexyl, cycloheptyl, bicyclopentanyl, bicyclohexanyl or bicycloheptanyl, each being optionally partially or fully halogenated and optionally substituted with one to three $C_{1-3}$ alkyl optionally partially or fully halogenated, nitrile, hydroxy$C_{1-3}$alkyl or aryl;

$C_{3-10}$ branched or unbranced alkenyl each being optionally partially or fully halogenated, and optionally substituted with one to three $C_{1-5}$ branched or unbranched alkyl, phenyl, naphthyl, cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

oxo, nitrile, halogen; or $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl) amino optionally substituted by one or more halogen atoms;

each $R_2$, $R_4$, and $R_5$ is a $C_{1-6}$ branched or unbranched alkyl optionally partially or fully halogenated, $C_{1-6}$acyl, aroyl, $C_{1-4}$ branched or unbranched alkoxy, each being optionally partially or fully halogenated, halogen, methoxycarbonyl, $C_{1-4}$ alkyl-$S(O)_m$ branched or unbranched and optionally partially or fully halogenated, or phenyl-$S(O)_m$;

$R_3$ which is covalently attached to G, is wherein for $R_3$:

$R_a$ and $R_b$ are each independently: hydrogen, a $C_{1-10}$ saturated or unsaturated branched or unbranched carbon chain, wherein one of the C atoms is optionally replaced by O or N and optionally substituted by oxo;

or $R_a$ and $R_b$ are each independently $C_{3-7}$ cycloalkyl$C_{0-6}$ alkyl, phenyl$C_{0-6}$ alkyl, heterocycle$C_{0-6}$ alkyl or heteroaryl$C_{0-6}$ alkyl wherein the $C_{0-6}$ alkyl portion for each is optionally substituted by oxo and wherein the heterocycle or heteroaryl moiety is chosen from morpholino, pyridinyl, piperadinyl, piperazinyl, pyrimidinyl, pyrazinyl, pyridazinyl, pyrrolyl, pyrrolidinyl, imidazolyl, pyrazolyl, thiazolyl, oxazolyl, oxazoyl, [1,3,4]oxadiazol, triazolyl, tetrazolyl, isoxazolyl, isothiazolyl, quinolinyl, isoquinolinyl, indolyl, benzimidazolyl, benzoxazolyl, benzisoxazolyl, benzpyrazolyl, quinoxalinyl, quinazolinyl and indazolyl, each $C_{3-7}$ cycloalkyl, phenyl, heterocycle or heteroaryl is optionally substituted by $C_{1-6}$ alkyl, halogen, hydroxy, carboxy, oxo, amino, imino, nitro or nitrile;

or $R_a$ and $R_b$ together with the nitrogen atom to which they are attached form a morpholino, pyridinyl, piperadinyl, piperazinyl, pyrimidinyl, pyrazinyl, pyridazinyl, pyrrolyl, pyrrolidinyl, imidazolyl, pyrazolyl, thiazolyl, oxazolyl, oxazoyl, [1,3,4]oxadiazol, triazolyl, tetrazolyl, isoxazolyl, isothiazolyl, quinolinyl, isoquinolinyl, indolyl, benzimidazolyl, benzoxazolyl, benzisoxazolyl, benzpyrazolyl, cinnolinyl, pterindinyl, phthalazinyl, naphthypyridinyl, quinoxalinyl, quinazolinyl, purinyl or indazolyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl and cyclohexanoimidazolyl, wherein each of the above is optionally substituted by one to three $R_6$. wherein $R_6$ is chosen from oxo, halogen, nitro, hydoxy, carboxy nitrile, amino, imino, guanidino, phenyl or $C_{1-4}$ alkyl optionally substituted by one or more halogen atoms;

$R_7$ is hydrogen or $C_{1-6}$ branched or unbranched alkyl optionally partially or fully halogenated, m is 0, 1, 2 or 3;

and

W is O or S or the pharmaceutically acceptable derivatives thereof.

In a first subgeneric aspect of the invention there is provided compounds of the formula(I) as described above and wherein:

$R_3$ is $R_7$ is hydrogen;

E is —NH—; and

W is O.

In yet another embodiment there are provided compounds of the formula(I) as described immediately above and wherein:

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen; and Z is:

phenyl, heteroaryl selected from pyridinyl, piperazinyl, pyrimidinyl, pyridazinyl, pyrazinyl, imidazolyl, furanyl, thienyl and pyranyl, heterocycle selected from 2-oxa-5-aza-bicyclo[2.2.1]heptanyl, tetrahydropyrimidonyl, pentamethylene sulfidyl, pentamethylene sulfoxidyl, pentamethylene sulfonyl, tetramethylene sulfidyl, tetramethylene sulfoxidyl tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, piperidinyl, piperidinonyl, dihydrothiazolyl, dihydrothiazolyl sulfoxidyl, pyrrolidinyl and dioxolanyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

or Z is optionally substituted by phenyl, heterocycle or heteroaryl as hereinabove described in this paragraph each in turn is optionally substituted by halogen, $C_{1-3}$ alkyl or $C_{1-3}$ alkoxy; or Z is hydroxy, halogen, nitrile, amino wherein the N atom is optionally independently mono- or di-substituted by $C_{1-3}$ acyl, $C_{1-6}$ alkyl or $C_{1-3}$ alkoxy$C_{1-3}$ alkyl, $C_{1-6}$ alkyl branched or unbranched, $C_{1-6}$ alkoxy, $C_{1-3}$ acylamino, nitrile$C_{1-4}$ alkyl, $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino.

In yet still another embodiment of the invention there is provided compounds of the formula(I) as described immediately above and wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, benzooxazolyl, indanyl, indolyl, indolinyl, indolonyl or indolinonyl, wherein G is substituted by one $R_3$ and further substituted by one or more $R_1$ or $R_2$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl) amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated carbon chain wherein one or more of the C atoms is optionally replaced by O, N or S and wherein Y is optionally independently substituted with nitrile or oxo;

Z is:

phenyl, pyridinyl, pyrimidinyl, pyridazinyl, pyrazinyl, imidazolyl, dihydrothiazolyl, dihydrothiazolyl sulfoxide, pyranyl, pyrrolidinyl, phenylpiperazinyl, tetrahydropyranyl, tetrahydrofuranyl, dioxolanyl, 2-oxa-5-aza-bicyclo[2.2.1] heptanyl, morpholino, thiomorpholino, thiomorpholino sulfoxidyl, piperidinyl, piperidinonyl, piperazinyl or tetrahydropyrimidonyl each of which are optionally substituted with one to two $C_{1-2}$ alkyl or $C_{1-2}$ alkoxy; or Z is hydroxy, $C_{1-3}$ alkyl, $C_{1-3}$ alkoxy, $C_{1-3}$ acylamino, $C_{1-3}$ alkylsulfonyl, nitrile $C_{1-3}$ alkyl or amino mono or di-substituted by $C_{1-3}$ acyl, $C_{1-6}$ alkyl or $C_{1-3}$ alkoxy$C_{1-3}$ alkyl;

each $R_1$ is independently:

$C_{1-5}$ alkyl branched or unbranched optionally partially or fully halogenated, wherein one or more C atoms are optionally independently replaced by O, N or $S(O)_m$, and wherein said $C_{1-5}$ alkyl is optionally substituted with oxo, cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; oxo;

$C_{2-4}$ alkynyl optionally partially or fully halogenated wherein one or more methylene groups are optionally replaced by O, and optionally independently substituted with one to two oxo groups, hydroxy, $C_{1-4}$ alkyl optionally substituted by one or more halogen atoms, nitrile, or mono- or di($C_{1-3}$alkyl)amino optionally substituted by one or more halogen atoms;

each $R_2$ is independently:

a $C_{1-4}$ alkyl optionally partially or fully halogenated, $C_{1-4}$ alkoxy optionally partially or fully halogenated, bromo, chloro, fluoro, methoxycarbonyl, methyl-$S(O)_m$, ethyl-$S(O)_m$ each optionally partially or fully halogenated or phenyl-$S(O)_m$;

In yet a further embodiment of the invention there is provided compounds of the formula(I) as described immediately above and wherein:

G is:

phenyl, pyridinyl, pyridonyl, 2-naphthyl, quinolinyl, isoquinolinyl, dihydrobenzofuranyl, indanyl, 5-indolyl, indolinyl, indolonyl, or indolinonyl, wherein G is substituted by one $R_3$ and further substituted by one or more $R_1$ or $R_2$;

Ar is 1-naphthyl;

X is:

phenyl, imidazolyl, pyridinyl, pyrimidinyl, piperdinyl, piperazinyl, pyridazinyl or pyrazinyl and wherein X is attached to the 4-position of Ar;

Y is:

a bond or

—$CH_2$—, —$CH_2CH_2$—, O—$CH_2CH_2$—, —C(O)—, —O—, —S—, —NH—$CH_2CH_2$—, —N($CH_3$)—, $CH_2$(CN)$CH_2$—NH—$CH_2$ or —NH—;

Z is:

morpholinyl, thiomorpholinyl, thiomorpholinyl sulfoxidyl, dioxolanyl, tetrahydrofuranyl, pyridinyl, $C_{1-3}$ acylamino, $C_{1-6}$ dialkylamino, $C_{1-3}$ alkylsulfonyl or nitrile$C_{1-3}$ alkyl;

$R_1$ is:

$C_{1-5}$ alkyl optionally partially or fully halogenated wherein one or more C atoms are optionally independently replaced by O or N, and wherein said $C_{1-5}$ alkyl is optionally substituted with oxo,;

cyclopropyl, cyclopentanyl, cyclohexanyl and bicyclopentanyl optionally substituted with one to three methyl groups optionally partially or fully halogenated, nitrile, hydroxymethyl or phenyl;

$R_2$ is:

$C_{1-4}$ alkoxy optionally partially or fully halogenated, bromo, chloro, fluoro, nitrile, nitro, amino,; and $R_a$ and $R_b$ are each independently hydrogen, $C_{1-5}$ alkyl, phenyl$C_{0-5}$ alkyl optionally substituted on the phenyl by $C_{1-6}$ alkyl, halogen, hydroxy, carboxy, oxo, amino, imino, nitro or nitrile;

or $R_a$ and $R_b$ together with the nitrogen atom to which they are attached form a morpholino, piperidinyl, piperazinyl, pyridinyl, pyrimidinyl, pyrazinyl, pyridazinyl, pyrrolyl, pyrrolidinyl, imidazolyl, pyrazolyl, oxazolyl, isoxazolyl and isothiazolyl, each optionally substituted by one to two $R_6$;

In yet still a further embodiment of the invention there are provided compounds of the formula(I) as described immediately above and wherein:

G is:

phenyl or pyridinyl wherein G is substituted by one $R_3$ and further substituted by one or more $R_1$ or $R_2$;

X is:

phenyl, imidazolyl, pyridinyl, pyrimidinyl or pyrazinyl;

Y is:

a bond, —OCH$_2$CH$_2$—, —CH$_2$CH$_2$—, —O—, CH$_2$(CN) CH$_2$—NH—CH$_2$, —CH$_2$—, —NH—CH$_2$CH$_2$— or —NH—;

Z is:

morpholin-4yl, thiomorpholin-4-yl, thiomorpholin-4-yl sulfoxidyl, piperidin-1-yl, dimethylamino, tetrahydrofuranyl, pyridinyl or di-$C_{1-3}$ alkylamino;

$R_1$ is:

tert-butyl, sec-butyl, phenyl, or cyclohexanyl;

$R_a$ and $R_b$ are each independently hydrogen, a $C_{1-4}$ alkyl, phenyl, benzyl wherein the phenyl or phenyl portion of the benzyl are optionally substituted by methyl, halogen, hydroxy, carboxy, amino;

or $R_a$ and $R_b$ together with the nitrogen atom to which they are attached form a morpholino, piperidinyl, piperazinyl or pyrrolidinyl, each optionally substituted by one to two $R_6$;

and $R_6$ is $C_{1-4}$ alkyl, halogen, nitro, nitrile, hydoxy, carboxy or oxo.

In yet still even a further embodiment of the invention there is provided compounds of the formula(I) as described immediately above and wherein:

G is phenyl substituted by $R_3$ and one to two $R_1$ or $R_2$;

X is phenyl or pyridin-3yl;

$R_a$ and $R_b$ are each independently hydrogen, a $C_{1-3}$ alkyl, phenyl or benzyl;

or $R_a$ and $R_b$ together with the nitrogen atom to which they are attached form a morpholino, piperidinyl, piperazinyl or pyrrolidinyl, each optionally substituted by one to two $R_6$;

and $R_6$ is $C_{1-3}$ alkyl or halogen.

Y is:

a bond, —OCH$_2$CH$_2$—, —CH$_2$CH$_2$—, —O—, —CH$_2$—, —NH—CH$_2$CH$_2$— or —NH—;

Z is morpholin-4yl, thiomorpholin-4-yl, thiomorpholin-4-yl sulfoxidyl, piperidin-1-yl or dimethylamino;

In still even a further embodiment of the invention there is provided compounds of the formula(I) as provided immediately above and wherein:

the attachment of X to Ar and Y is at the following X positions: 3-,6-pyridinyl or 1-,4-phenyl, respectively;

Y is —CH$_2$— and $R_6$ is methyl or ethyl.

A preferred compound embraced by the first subgeneric aspect of the formula(I) is:

or the pharmaceutically acceptable derivatives thereof.

In addition to the abovementioned compound, the following compounds of the formula(I) may be made by the general methods described in the specification:

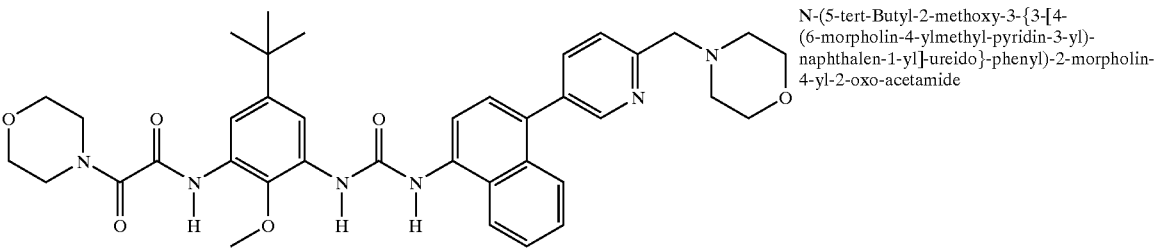

N-(5-tert-Butyl-2-methoxy-3-{3-[4-(6-morpholin-4-ylmethyl-pyridin-3-yl)-naphthalen-1-yl]-ureido}-phenyl)-2-morpholin-4-yl-2-oxo-acetamide

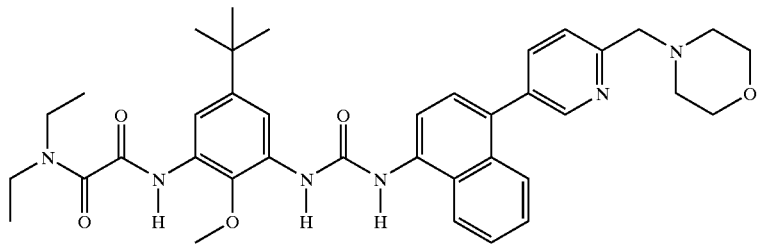

N-(5-tert-Butyl-2-methoxy-3-{3-[4-(6-morpholin-4-ylmethyl-pyridin-3-yl)-naphthalen-1-yl]-ureido}-phenyl)-N',N'-diethyl-oxalamide;

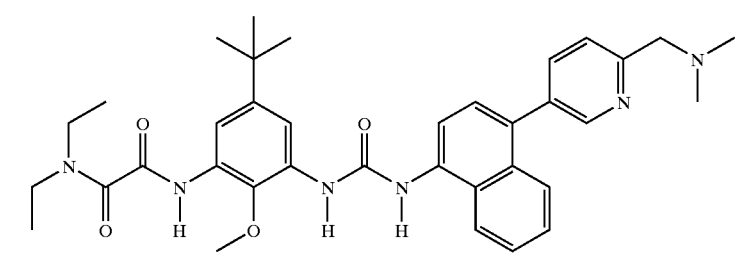

N-(5-tert-Butyl-3-{3-[4-(6-dimethylaminomethyl-pyridin-3-yl)-naphthalen-1-yl]-ureido}-2-methoxy-phenyl)-N',N'-diethyl-oxalamide;

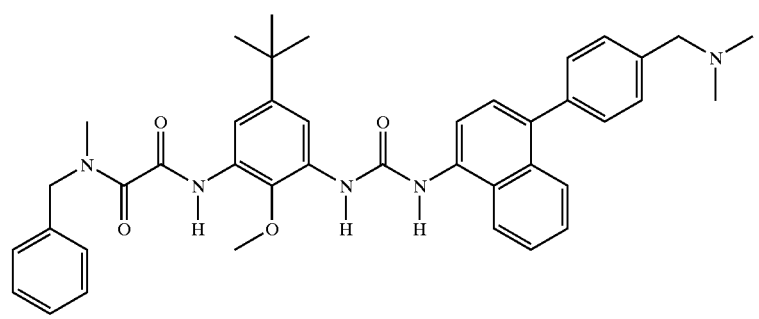

N-Benzyl-N'-(5-tert-butyl-3-{3-[4-(4-dimethylaminomethyl-phenyl)-naphthalen-1-yl]-ureido}-2-methoxy-phenyl)-N-methyl-oxalamide;

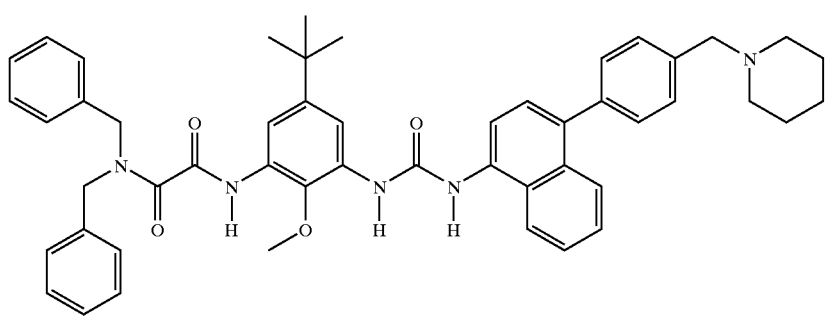

N,N-Dibenzyl-N'-(5-tert-butyl-2-methoxy-3-{3-[4-(4-piperidin-1-ylmethyl-phenyl)-naphthalen-1-yl]-ureido}-phenyl)-oxalamide;

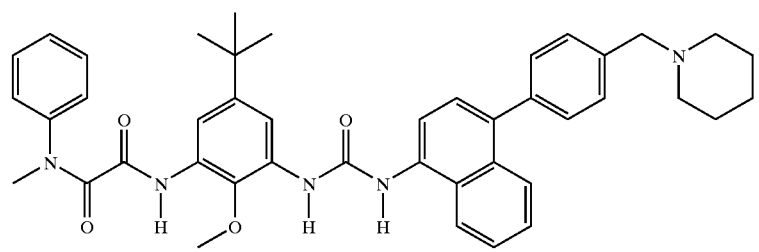

N-(5-tert-Butyl-2-methoxy-3-{3-[4-(4-piperidin-1-ylmethyl-phenyl)-naphthalen-1-yl]-ureido}-phenyl)-N'-methyl-N'-phenyl-oxalamide;

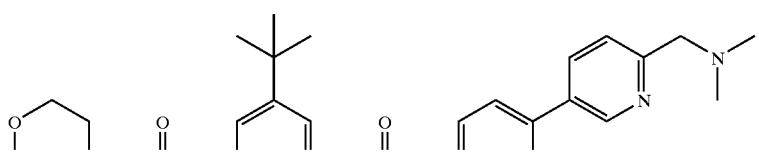

N-(5-tert-Butyl-3-{3-[4-(6-dimethylaminomethyl-pyridin-3-yl)-naphthalen-1-yl]-ureido}-2-methoxy-phenyl)-2-morpholin-4-yl-2-oxo-acetamide;

or the pharmaceutically acceptable derivatives thereof.

In a second subgeneric aspect of the invention there is provided compounds of the formula(I) as described in the broadest generic aspect above and wherein:

$R_3$ which is covalently attached to G, is

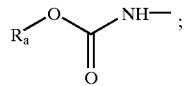

E is —NH— and
W is O.

In yet another embodiment there are provided compounds of the formula(I) as described immediately above and wherein:

Ar is:
naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-S(O)$_m$ or halogen; and Z is:
phenyl, heteroaryl selected from pyridinyl, piperazinyl, pyrimidinyl, pyridazinyl, pyrazinyl, imidazolyl, furanyl, thienyl and pyranyl, heterocycle selected from 2-oxa-5-aza-bicyclo[2.2.1]heptanyl, tetrahydropyrimidonyl, pentamethylene sulfidyl, pentamethylene sulfoxidyl, pentamethylene sulfonyl, tetramethylene sulfidyl, tetramethylene sulfoxidyl tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, piperidinyl, piperidinonyl, dihydrothiazolyl, dihydrothiazolyl sulfoxidyl, pyrrolidinyl and dioxolanyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

or Z is optionally substituted by phenyl, heterocycle or heteroaryl as hereinabove described in this paragraph each in turn is optionally substituted by halogen, $C_{1-3}$ alkyl or $C_{1-3}$ alkoxy; or Z is hydroxy, halogen, nitrile, amino wherein the N atom is optionally independently mono- or di-substituted by $C_{1-3}$ acyl, $C_{1-6}$ alkyl or $C_{1-3}$ alkoxy$C_{1-3}$ alkyl, $C_{1-6}$ alkyl branched or unbranched, $C_{1-6}$ alkoxy, $C_{1-3}$ acylamino, nitrile$C_{1-4}$ alkyl, $C_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino.

$R_a$ is a $C_{1-10}$ saturated or unsaturated branched or unbranched carbon chain, wherein one of the C atoms is optionally replaced by O or N and optionally substituted by oxo;

or $R_a$ is $C_{3-7}$ cycloalkyl$C_{0-6}$ alkyl, phenyl$C_{0-6}$ alkyl, heterocycle$C_{0-6}$ alkyl or heteroaryl$C_{0-6}$ alkyl wherein the $C_{0-6}$ alkyl portion is optionally substituted by oxo and wherein the heterocycle or heteroaryl moiety is chosen from morpholino, pyridinyl, piperidinyl, piperazinyl, pyrimidinyl, pyrazinyl, pyridazinyl, pyrrolyl, pyrrolidinyl, imidazolyl, pyrazolyl, thiazolyl, oxazolyl, oxazoyl, [1,3,4]oxadiazol, triazolyl, tetrazolyl, isoxazolyl and isothiazolyl, each $C_{3-7}$ cycloalkyl, phenyl, heterocycle or heteroaryl is optionally substituted by $C_{1-6}$ alkyl, halogen, hydroxy, carboxy, oxo, amino, nitro or nitrile;

In yet still another embodiment of the invention there is provided compounds of the formula(I) as described immediately above and wherein:

G is
phenyl, pyridinyl, pyridonyl, naphthyl, quinolinyl, isoquinolinyl, pyrazinyl, 3,4-dihydro-2H-benzo[1,4] oxazinyl, benzothiophenyl, dihydrobenzofuranyl, dihydrobenzothiophenyl, benzooxazolyl, indanyl, indolyl, indolinyl, indolonyl or indolinonyl, wherein G is substituted by one $R_3$ and further substituted by one or more $R_1$ or $R_2$;

Ar is naphthyl;

X is
phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$ alkoxy, hydroxy, nitrile, amino, mono- or di-($C_{1-3}$ alkyl) amino, mono- or di-($C_{1-3}$ alkylamino)carbonyl, $NH_2C(O)$, $C_{1-6}$ alkyl-S(O)$_m$ or halogen;

Y is:
a bond or
a $C_{1-4}$ saturated carbon chain wherein one or more of the C atoms is optionally replaced by O, N or S and wherein Y is optionally independently substituted with nitrile or oxo;

Z is:
phenyl, pyridinyl, pyrimidinyl, pyridazinyl, pyrazinyl, imidazolyl, dihydrothiazolyl, dihydrothiazolyl sulfoxide, pyranyl, pyrrolidinyl, phenylpiperazinyl, tetrahydropyranyl, tetrahydrofuranyl, dioxolanyl, 2-oxa-5-aza-bicyclo[2.2.1]heptanyl, morpholino, thiomorpholino, thiomorpholino sulfoxidyl, piperidinyl, piperidinonyl, piperazinyl or tetrahydropyrimidonyl each of which are optionally substituted with one to two $C_{1-2}$ alkyl or $C_{1-2}$ alkoxy; or Z is amino mono or di-substituted by $C_{1-3}$ acyl, $C_{1-6}$ alkyl or $C_{1-3}$ alkoxy$C_{1-3}$ alkyl;

each $R_1$ is independently:
$C_{1-5}$ alkyl branched or unbranched optionally partially or fully halogenated, wherein one or more C atoms are optionally independently replaced by O, N or S(O)$_m$, and wherein said $C_{1-5}$ alkyl is optionally substituted with oxo, dioxolanyl, pyrrolidinyl, furyl or phenyl each optionally substituted with one to three halogen, $C_{1-3}$ alkyl which is optionally partially or fully halogenated, hydroxy, nitrile and $C_{1-3}$ alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; oxo;

$C_{2-4}$ alkynyl optionally partially or fully halogenated wherein one or more methylene groups are optionally replaced by O, and optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$ is independently:
a $C_{1-4}$ alkyl optionally partially or fully halogenated, $C_{1-4}$ alkoxy optionally partially or fully halogenated, bromo, chloro, fluoro, methoxycarbonyl, methyl-S(O)$_m$, ethyl-S(O)$_m$ each optionally partially or fully halogenated or phenyl-S(O)$_m$;

or $R_2$ is mono- or di-$C_{1-3}$acylamino, amino-$S(O)_m$ or $S(O)_m$amino wherein the N atom is mono- or di-substituted by $C_{1-3}$alkyl or phenyl, nitrile, nitro or amino;

In yet a further embodiment of the invention there is provided compounds of the formula(I) as described immediately above and wherein:

G is:

phenyl, pyridinyl, pyridonyl, 2-naphthyl, quinolinyl, isoquinolinyl, dihydrobenzofuranyl, indanyl, 5-indolyl, indolinyl, indolonyl, or indolinonyl, wherein G is substituted by one $R_3$ and further substituted by one or more $R_1$ or $R_2$;

Ar is 1-naphthyl;

X is:

phenyl, imidazolyl, pyridinyl, pyrimidinyl, piperidinyl, piperazinyl, pyridazinyl or pyrazinyl and wherein X is attached to the 4-position of Ar;

Y is:

a bond or

—$CH_2$—, —$CH_2CH_2$—, O—$CH_2CH_2$—, >C(O), —O—, —S—, NH—$CH_2CH_2$—, —N($CH_3$)—, $CH_2$(CN)$CH_2$—NH—$CH_2$ or —NH—;

Z is:

morpholinyl, thiomorpholinyl, thiomorpholinyl sulfoxidyl, dioxolanyl, tetrahydrofuranyl, pyridinyl, piperazinyl each optionally substituted by $C_{1-2}$ alkyl or $C_{1-2}$ alkoxy; or Z is $C_{1-6}$ dialkylamino;

$R_1$ is:

$C_{1-5}$ alkyl optionally partially or fully halogenated wherein one or more C atoms are optionally independently replaced by O or N, and wherein said $C_{1-5}$ alkyl is optionally substituted with oxo, dioxolanyl, pyrrolidinyl, furyl or phenyl optionally substituted by $C_{1-3}$ alkoxy;

cyclopropyl, cyclopentanyl, cyclohexanyl and bicyclopentanyl optionally substituted with one to three methyl groups optionally partially or fully halogenated, nitrile, hydroxymethyl or phenyl; or 2-tetrahydrofuranyl substituted by methyl; propynyl substituted hydroxy or tetrahydropyran-2-yloxy;

$R_2$ is:

is $C_{1-4}$ alkoxy optionally partially or fully halogenated, mono- or di-$C_{1-3}$acylamino, amino-$S(O)_m$ or $S(O)_m$ amino wherein the N atom is mono- or di-substituted by $C_{1-3}$alkyl or phenyl, bromo, chloro, fluoro, nitrile, nitro, amino, methylsulfonyl optionally partially or fully halogenated or phenylsulfonyl;

$R_a$ is $C_{1-4}$ alkyl optionally substituted by $C_{1-3}$ alkoxy, mono- or di-$C_{1-3}$ alkylamino, mono- or di-$C_{1-3}$ alkylaminocarbonyl; or $R_a$ is heterocycle$C_{0-3}$ alkyl wherein the heterocycle is chosen from morpholinyl, tetrahydrofuranyl, pyrrolidinyl, 2,5-dioxo-pyrrolidinyl, piperidinyl, 2-oxo-piperidinyl and 3-oxo-morpholinyl, heteroaryl$C_{0-3}$ alkyl wherein the $C_{0-3}$ alkyl portion is optionally substituted by oxo and the heteroaryl is chosen from pyridinyl, imidazolyl, pyrazolyl, thiazolyl and oxazolyl or $R_a$ is $C_{3-6}$ cycloalkyl$C_{0-3}$ alkyl.

In yet still a further embodiment of the invention there are provided compounds of the formula(I) as described immediately above and wherein:

G is:

phenyl or pyridinyl, wherein G is substituted by one $R_3$ and further substituted by one or more $R_1$ or $R_2$;

X is:

phenyl, imidazolyl, pyridinyl, pyrimidinyl or pyrazinyl;

Y is:

a bond, —$OCH_2CH_2$—, —$CH_2CH_2$—, —O—, $CH_2$(CN) $CH_2$—NH—$CH_2$, —$CH_2$—, >C(O), —NH—$CH_2CH_2$— or —NH—;

Z is:

morpholinyl, thiomorpholinyl, thiomorpholinyl sulfoxidyl, tetrahydrofuranyl, pyridinyl, piperazinyl each optionally substituted by $C_{1-2}$ alkyl or $C_{1-2}$ alkoxy; or Z is $C_{1-3}$ dialkylamino;

$R_1$ is:

tert-butyl, sec-butyl, tert-amyl, phenyl, tetrahydropyran-2-yloxypropynyl, hydroxypropynyl, trihalomethyl, 2,2-diethylpropionyl or cyclohexanyl;

$R_2$ is:

$C_{1-4}$ alkoxy optionally partially or fully halogenated, chloro, nitro, amino, nitrile, methylsulfonylamino, diacetylamino, phenylsulfonylamino, N,N-di (methylsulfonyl)amino, methylsulfonyl or trihalomethylsulfonyl;

$R_a$ is $C_{1-4}$ alkyl optionally substituted by $C_{1-3}$ alkoxy, mono- or di-$C_{1-3}$ alkylamino, mono- or di-$C_{1-3}$ alkylaminocarbonyl; or $R_a$ is heterocycleC0–2 alkyl wherein the heterocycle is chosen from morpholinyl, tetrahydrofuranyl, pyrrolidinyl, 2,5-dioxo-pyrrolidinyl, piperidinyl, 2-oxo-piperidinyl and 3-oxo-morpholinyl, heteroarylC0–2 alkyl wherein the heteroaryl is chosen from piperidinyl and oxazolyl or $R_a$ is $C_{3-6}$ cycloalkyl $C_{0-2}$ alkyl;

In yet still even a further embodiment of the invention there is provided compounds of the formula(I) as described immediately above and wherein:

G is phenyl substituted by $R_3$ and one to two $R_1$ or $R_2$;

X is phenyl, pyridinyl, pyrimidinyl or pyrazinyl;

$R_a$ is $C_{1-4}$ alkyl optionally substituted by $C_{1-3}$ alkoxy, mono- or di-$C_{1-3}$ alkylamino, mono- or di-$C_{1-3}$ alkylaminocarbonyl; or $R_a$ is heterocycle$C_{0-2}$ alkyl wherein the heterocycle is chosen from morpholin-4-yl, tetrahydrofuran-2-yl, pyrrolidin-1 or 2-yl, 2,5-dioxo-pyrrolidin-1-yl, piperidin-2-yl, 2-oxo-piperidin-3-yl and 3-oxo-morpholin-4-yl, heteroaryl$C_{0-2}$ alkyl wherein the heteroaryl is chosen from piperidin-3 or 4-yl and oxazol-5-yl or $R_a$ is cyclopropylmethyl;

Y is:

—O—, —$CH_2$— or >C(O);

Z is morpholin-4-yl, thiomorpholin-4-yl, thiomorpholin-4-yl sulfoxidyl, piperazin-1-yl each optionally substituted by $C_{1-2}$ alkyl; or Z is $C_{1-2}$ dialkylamino.

In still even a further embodiment of the invention there is provided compounds of the formula(I) as provided immediately above and wherein:

the attachment of X to Ar and Y is at the following X positions: 3,6 pyridinyl, 1,4 phenyl, 2,5 pyrimidinyl and 2,5 pyrazinyl, respectively;

Y is —$CH_2$— or >C(O).

Table II shows representative compounds embraced by the second subgeneric aspect of the formula(I):

TABLE II

| Structure | Name |
|---|---|
| (structure) | (5-tert-Butyl-2-methoxy-3-{3-[4-(6-morpholin-4-ylmethyl-pyridin-3-yl)-naphthalen-1-yl]-ureido}-phenyl)-carbamic acid methyl ester; |
| (structure) | (5-tert-Butyl-2-methoxy-3-{3-[4-(6-morpholin-4-ylmethyl-pyridin-3-yl)-naphthalen-1-yl]-ureido}-phenyl)-carbamic acid isopropyl ester; |
| (structure) | (5-tert-Butyl-2-methoxy-3-{3-[4-(6-morpholin-4-ylmethyl-pyridin-3-yl)-naphthalen-1-yl]-ureido}-phenyl)-carbamic acid 2-methoxy-ethyl ester; |
| (structure) | (5-tert-Butyl-2-methoxy-3-{3-[4-(6-morpholin-4-ylmethyl-pyridin-3-yl)-naphthalen-1-yl]-ureido}-phenyl)-carbamic acid ethyl ester; |
| (structure) | (5-tert-Butyl-2-methoxy-3-{3-[4-(6-morpholin-4-ylmethyl-pyridin-3-yl)-naphthalen-1-yl]-ureido}-phenyl)-carbamic acid 2-morpholin-4-yl-ethyl ester | or the pharmaceutically acceptable derivatives thereof.

In addition to the abovementioned compounds, the following compounds of the formula(I) may be made by the general methods described in the specification:

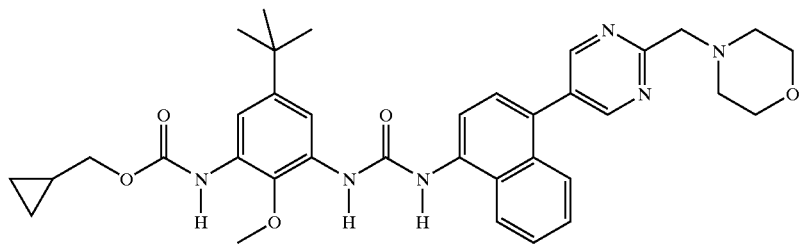

(5-tert-Butyl-2-methoxy-3-{3-[4-(2-morpholin-4-ylmethyl-pyrimidin-5-yl)-naphthalen-1-yl]-ureido}-phenyl)-carbamic acid cyclopropylmethyl ester;

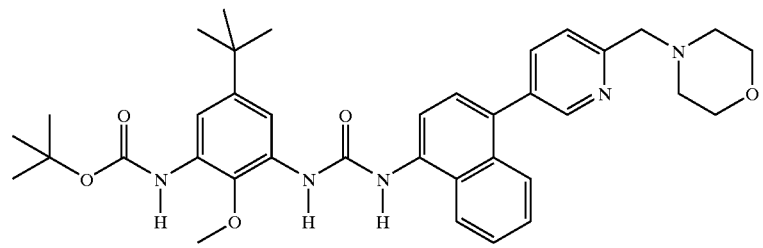

(5-tert-Butyl-2-methoxy-3-{3-[4-(6-morpholin-4-ylmethyl-pyrimidin-3-yl)-naphthalen-1-yl]-ureido}-phenyl)-carbamic acid tert-butyl ester;

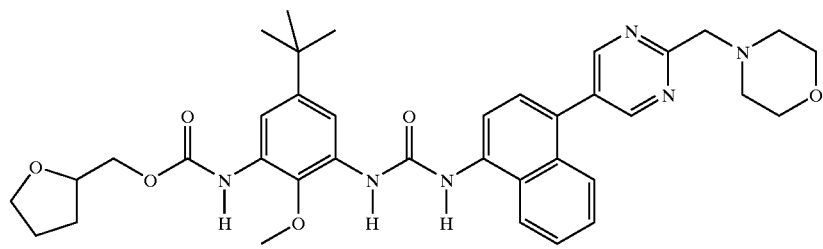

(5-tert-Butyl-2-methoxy-3-{3-[4-(2-morpholin-4-ylmethyl-pyrimidin-5-yl)-naphthalen-1-yl]-ureido}-phenyl)-carbamic acid tetrahydro-furan-2-ylmethyl ester;

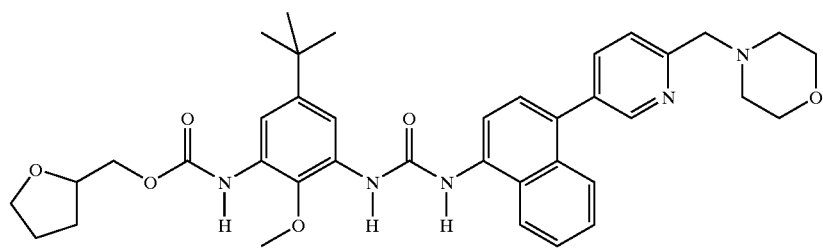

(5-tert-Butyl-2-methoxy-3-{3-[4-(6-morpholin-4-ylmethyl-pyridin-3-yl)-naphthalen-1-yl]-ureido}-phenyl)-carbamic acid tetrahydro-furan-2-ylmethyl ester;

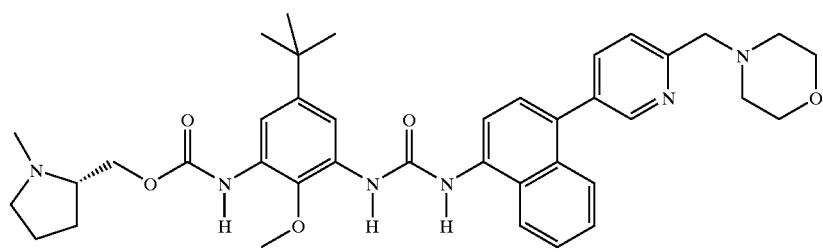

(5-tert-Butyl-2-methoxy-3-{3-[4-(6-morpholin-4-ylmethyl-pyrimidin-3-yl)-naphthalen-1-yl]-ureido}-phenyl)-carbamic acid 1-methyl-pyrrolidin-2-ylmethyl ester;

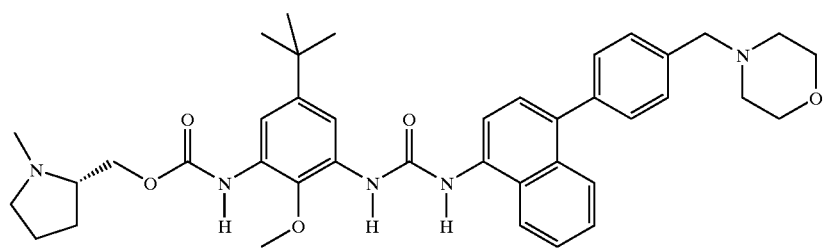

(5-tert-Butyl-2-methoxy-3-{3-[4-(4-morpholin-4-ylmethyl-phenyl)-naphthalen-1-yl]-ureido}-phenyl)-carbamic acid 1-methyl-pyrrolidin-2-ylmethyl ester;

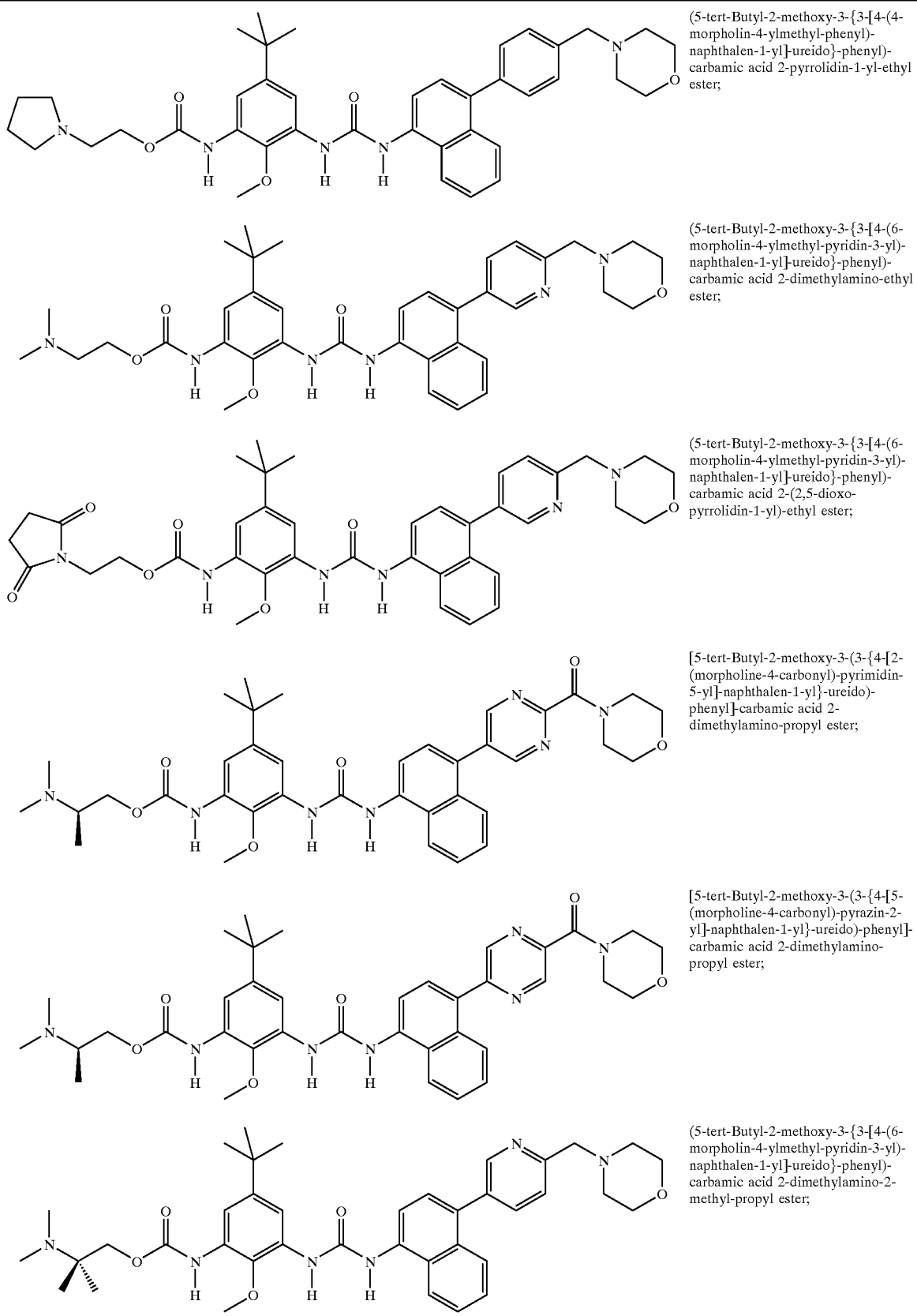

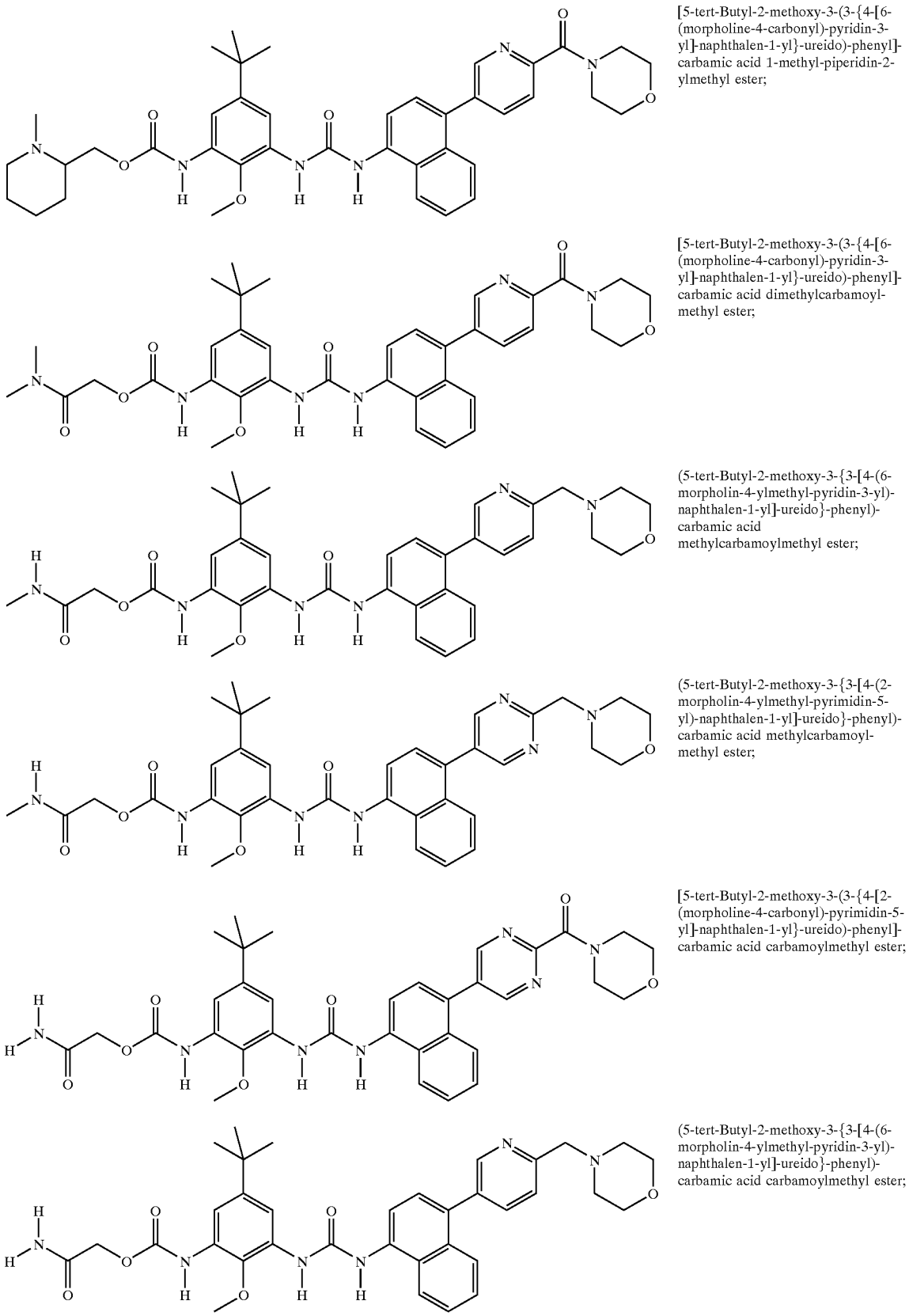

[5-tert-Butyl-2-methoxy-3-(3-{4-[6-(morpholine-4-carbonyl)-pyridin-3-yl]-naphthalen-1-yl}-ureido)-phenyl]-carbamic acid 1-methyl-piperidin-2-ylmethyl ester;

[5-tert-Butyl-2-methoxy-3-(3-{4-[6-(morpholine-4-carbonyl)-pyridin-3-yl]-naphthalen-1-yl}-ureido)-phenyl]-carbamic acid dimethylcarbamoyl-methyl ester;

(5-tert-Butyl-2-methoxy-3-{3-[4-(6-morpholin-4-ylmethyl-pyridin-3-yl)-naphthalen-1-yl]-ureido}-phenyl)-carbamic acid methylcarbamoylmethyl ester;

(5-tert-Butyl-2-methoxy-3-{3-[4-(2-morpholin-4-ylmethyl-pyrimidin-5-yl)-naphthalen-1-yl]-ureido}-phenyl)-carbamic acid methylcarbamoyl-methyl ester;

[5-tert-Butyl-2-methoxy-3-(3-{4-[2-(morpholine-4-carbonyl)-pyrimidin-5-yl]-naphthalen-1-yl}-ureido)-phenyl]-carbamic acid carbamoylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid carbamoylmethyl ester;

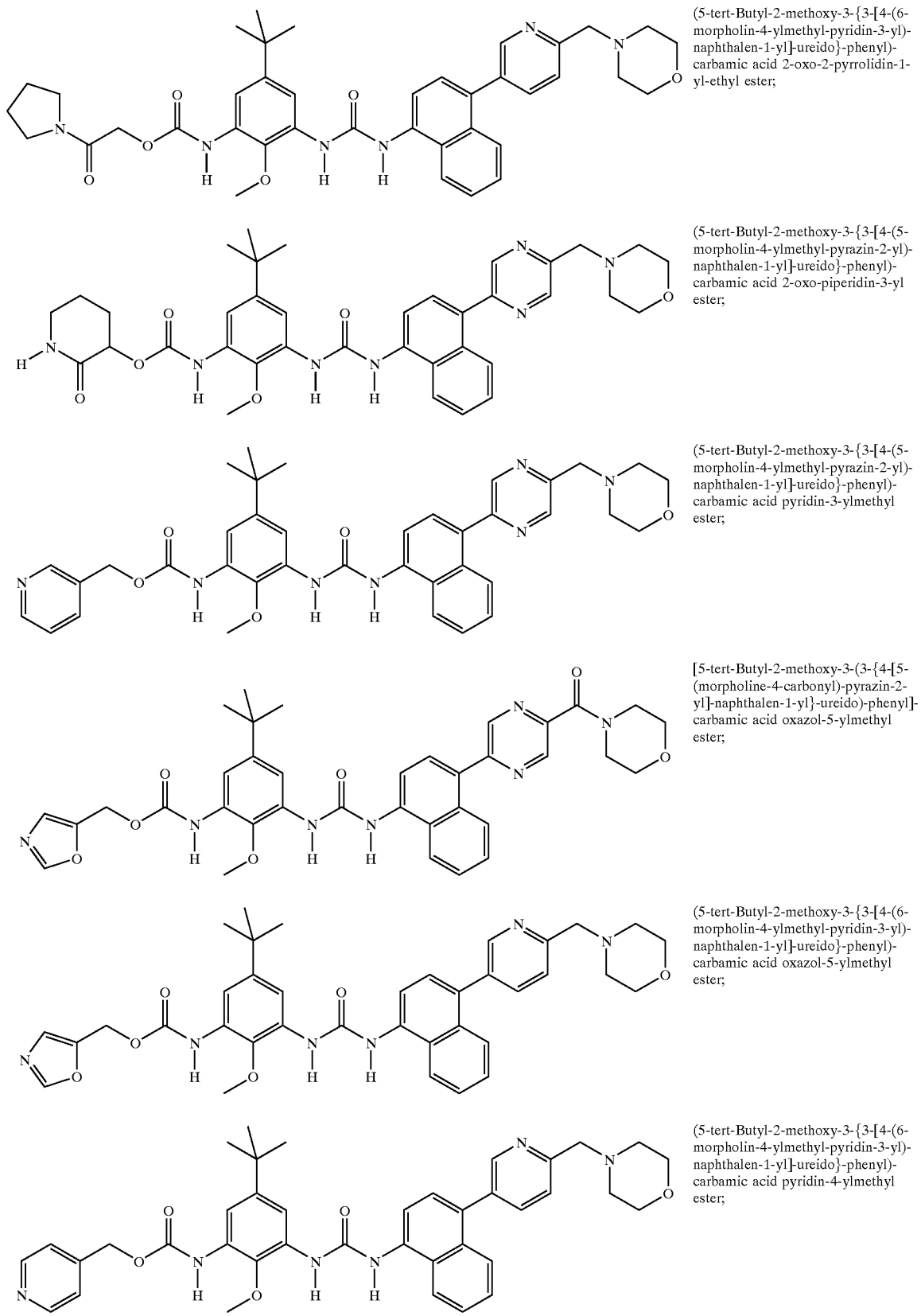

(5-tert-Butyl-2-methoxy-3-{3-[4-(6-morpholin-4-ylmethyl-pyridin-3-yl)-naphthalen-1-yl]-ureido}-phenyl)-carbamic acid 2-oxo-2-pyrrolidin-1-yl-ethyl ester;

(5-tert-Butyl-2-methoxy-3-{3-[4-(5-morpholin-4-ylmethyl-pyrazin-2-yl)-naphthalen-1-yl]-ureido}-phenyl)-carbamic acid 2-oxo-piperidin-3-yl ester;

(5-tert-Butyl-2-methoxy-3-{3-[4-(5-morpholin-4-ylmethyl-pyrazin-2-yl)-naphthalen-1-yl]-ureido}-phenyl)-carbamic acid pyridin-3-ylmethyl ester;

[5-tert-Butyl-2-methoxy-3-(3-{4-[5-(morpholine-4-carbonyl)-pyrazin-2-yl]-naphthalen-1-yl}-ureido)-phenyl]-carbamic acid oxazol-5-ylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid oxazol-5-ylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid pyridin-4-ylmethyl ester;

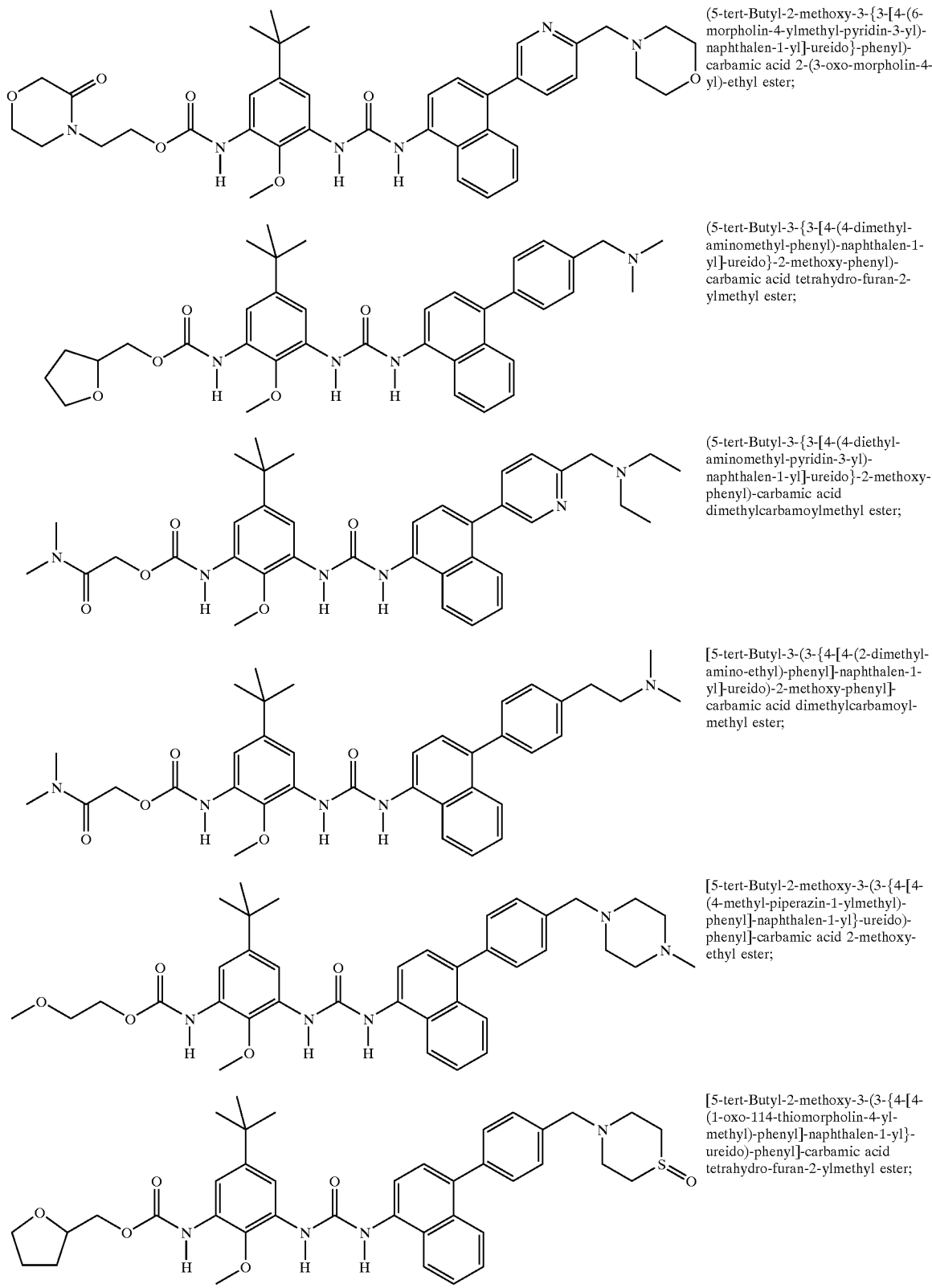

(5-tert-Butyl-2-methoxy-3-{3-[4-(6-morpholin-4-ylmethyl-pyridin-3-yl)-naphthalen-1-yl]-ureido}-phenyl)-carbamic acid 2-(3-oxo-morpholin-4-yl)-ethyl ester;

(5-tert-Butyl-3-{3-[4-(4-dimethyl-aminomethyl-phenyl)-naphthalen-1-yl]-ureido}-2-methoxy-phenyl)-carbamic acid tetrahydro-furan-2-ylmethyl ester;

(5-tert-Butyl-3-{3-[4-(4-diethyl-aminomethyl-pyridin-3-yl)-naphthalen-1-yl]-ureido}-2-methoxy-phenyl)-carbamic acid dimethylcarbamoylmethyl ester;

[5-tert-Butyl-3-(3-{4-[4-(2-dimethyl-amino-ethyl)-phenyl]-naphthalen-1-yl]-ureido)-2-methoxy-phenyl]-carbamic acid dimethylcarbamoyl-methyl ester;

[5-tert-Butyl-2-methoxy-3-(3-{4-[4-(4-methyl-piperazin-1-ylmethyl)-phenyl]-naphthalen-1-yl}-ureido)-phenyl]-carbamic acid 2-methoxy-ethyl ester;

[5-tert-Butyl-2-methoxy-3-(3-{4-[4-(1-oxo-1λ4-thiomorpholin-4-yl-methyl)-phenyl]-naphthalen-1-yl}-ureido)-phenyl]-carbamic acid tetrahydro-furan-2-ylmethyl ester;

or the pharmaceutically acceptable derivatives thereof.

From the above-listed compounds, the following are preferred:

(5-tert-Butyl-2-methoxy-3-{3-[4-(2-morpholin-4-ylmethyl-pyrimidin-5-yl)-naphthalen-1-yl]-ureido}-phenyl)-carbamic acid tetrahydro-furan-2-ylmethyl ester;
(5-tert-Butyl-2-methoxy-3-{3-[4-(6-morpholin-4-ylmethyl-pyridin-3-yl)-naphthalen-1-yl]-ureido}-phenyl)-carbamic acid tetrahydro-furan-2-ylmethyl ester;
[5-tert-Butyl-2-methoxy-3-(3-{4-[6-(morpholine-4-carbonyl)-pyridin-3-yl]-naphthalen-1-yl}-ureido)-phenyl]-carbamic acid dimethylcarbamoylmethyl ester;
(5-tert-Butyl-2-methoxy-3-{3-[4-(6-morpholin-4-ylmethyl-pyridin-3-yl)-naphthalen-1-yl]-ureido}-phenyl)-carbamic acid methylcarbamoylmethyl ester;
(5-tert-Butyl-2-methoxy-3-{3-[4-(5-morpholin-4-ylmethyl-pyrazin-2-yl)-naphthalen-1-yl]-ureido}-phenyl)-carbamic acid 2-oxo-piperidin-3-yl ester;
[5-tert-Butyl-2-methoxy-3-(3-{4-[5-(morpholine-4-carbonyl)-pyrazin-2-yl]-naphthalen-1-yl}-ureido)-phenyl]-carbamic acid oxazol-5-ylmethyl ester;
(5-tert-Butyl-2-methoxy-3-{3-[4-(6-morpholin-4-ylmethyl-pyridin-3-yl)-naphthalen-1-yl]-ureido}-phenyl)-carbamic acid oxazol-5-ylmethyl ester or the pharmaceutically acceptable derivatives thereof.

In all the compounds disclosed above, in the event the nomenclature is in conflict with the structure, it shall be understood that the compound is defined by the structure.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy and butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclobutenyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl, maleimidyl or 2-oxa- or 2-thia-5-aza-bicyclo[2.2.1]heptanyl and benzo or pyridino fused derivatives thereof.

The term "heteroaryl" shall be understood to mean an aromatic 3–8 membered monocyclic or 8–14 membered bicyclic ring containing 1–4 heteroatoms such as N,O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzothienyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl, and the mono or multiply saturated and benzo or pyridino fused derivatives thereof.

The term "aryl" as used herein shall be understood to mean aromatic carbocycle or heteroaryl as defined herein.

Terms which are analogs of the above cyclic moieties such as aryloxy or heteroaryl amine shall be understood to mean an aryl, heteroaryl, heterocycle as defined above attached to it's respective group.

All of the above-defined terms, where chemically possible, shall be understood to be optionally halogenated with one or more halogen atoms as defined below.

The term "halogen" as used in the present specification shall be understood to mean bromine, chlorine, fluorine or iodine.

The term "heteroatom" as used herein shall be understood to mean atoms other than carbon such as O, N, S and P.

As used herein, "nitrogen" and "sulfur" include any oxidized form of nitrogen and sulfur and the quaternized form of any basic nitrogen.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula(I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N-(C_1-C_4 \text{ alkyl})_4^+$ salts.

In addition, the compounds of this invention include prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a compound of the invention, thereby imparting the desired pharmacological effect.

Methods of Use

In accordance with the invention, there are provided methods of using the compounds of the formula (I). The compounds of the invention effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds of the invention are useful for the treatment of such conditions. These encompass diseases including, but not limited to, rheumatoid arthritis, osteoarthritis, traumatic arthritis, multiple sclerosis, Guillain-Barre syndrome, Crohn's disease, ulcerative colitis, psoriasis, graft versus host disease, systemic lupus erythematosus, glomerulonephritis, reperfusion injury, sepsis, bone resorption diseases including osteoporosis, chronic obstructive pulmonary disease, congestive heart failure, Alzheimer's disease, atherosclerosis, toxic shock syndrome, asthma, contact dermatitis, percutaneous transluminal coronary angioplasty (PTCA) and insulin-dependent diabetes mellitus.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention additionally provides for methods of making the compounds of the formula (I). The compounds of the invention may be prepared by the general methods and examples presented below, and methods known to those of ordinary skill in the art. Further reference in this regard may be made to U.S. Pat. Nos. 6,319,921 and 6,358,945, U.S. application Ser. Nos. 09/714,539, 09/611,109, 09/698,442, 09/834,797 and 09/902,085, and U.S. provisional application No. 60/283,642. Each of the aforementioned are incorporated herein by reference in their entirety.

In all schemes "G" in the formulas shown below shall have the meaning of "G" in the formula (I) of the invention described hereinabove.

The compounds of the invention may be prepared by Method A, B, C or D as illustrated in Scheme I, preferably Method C.

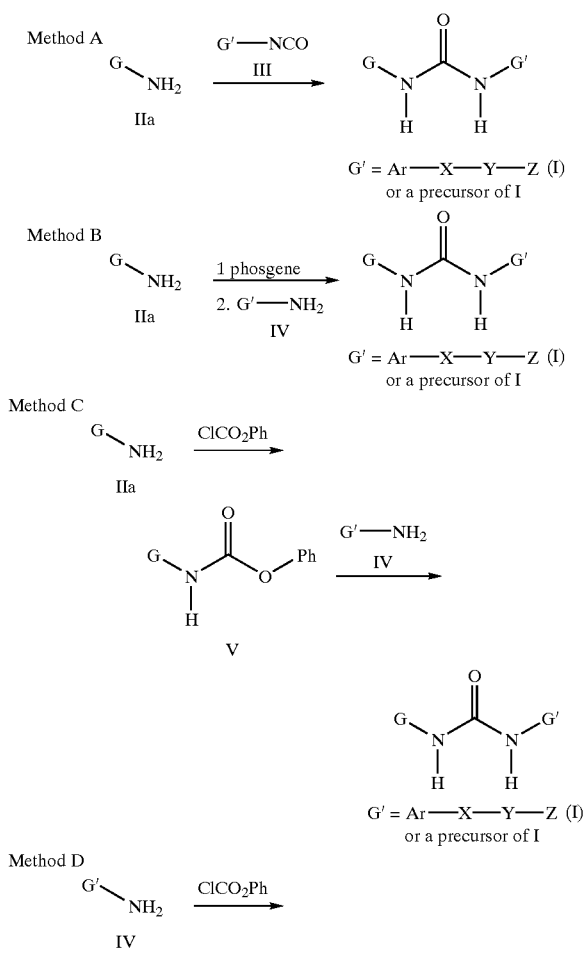

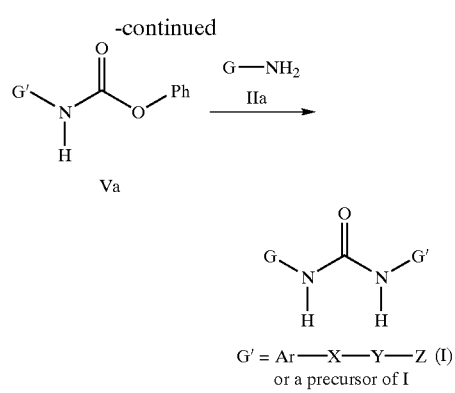

In Method A, a mixture of an arylamine of formula IIa and an arylisocyanate of formula III is dissolved in a non-protic, anhydrous solvent such as THF, ether, toluene, dioxane or ethyl acetate. The preferred solvent is THF. The mixture is stirred at between 0–45° C., preferably at 25° C., for 2–24 h, and the volatiles are removed. Purification of the residue by recrystallization from an appropriate solvent such as ethyl acetate/hexanes, ethyl acetate/MeOH, THF/petroleum ether, EtOH/water or by silica gel chromatography, using for example, hexanes and ethyl acetate as eluents, provides the product of formula I (E=NH) or precursors thereof.

In Method B, an arylamine of formula IIa is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 h, and the volatiles are removed. Purification of the residue by recrystallization or by silica gel chromatography, as above, provides the product of formula I (E=NH) or precursors thereof.

The required isocyanate may also be prepared from the carboxylic acid $G-CO_2H$ by reaction with a chloroformate, such as ethyl chloroformate, in the presence of a suitable base, such as triethylamine, in a suitable solvent, such as THF at about 0° C. The resulting mixed anhydride is treated with an aqueous solution of sodium azide. Heating a solution of the resulting acyl azide in a suitable solvent, such as toluene, at about reflux, results in a Curtius rearrangement, providing the isocyanate G—N=C=O in situ.

In Method C, an arylamine of formula IIa is dissolved in a suitable solvent such as a halogenated solvent which includes methylene chloride, chloroform or dichloroethane. The preferred solvent is methylene chloride. A suitable base such as triethylamine may be added, followed by an alkyl or aryl chloroformate, such as t-butyl chloroformate or phenyl chloroformate (shown). The mixture is stirred at between 0–85° C., preferably at reflux temperature, for 2–24 h, and the volatiles are removed providing carbamate V.

The carbamate and arylamine IV are mixed in a non-protic, anhydrous solvent such as THF, ether, toluene, dioxane, methylene chloride or ethyl acetate. The preferred solvent is THF. The mixture is stirred at between 0–110° C., preferably at reflux temperature, for 2–24 h, and the volatiles are removed. Purification of the residue as above provides the product of formula I (E=NH) or precursors thereof. This process can also be performed in the reverse sense as illustrated by Method D.

In Method D an arylamine of formula IV is dissolved in a suitable solvent such as a THF. A suitable alkyl or aryl chloroformate, such as t-butyl chloroformate or phenyl chloroformate (shown), is added. The mixture is stirred at between 0–85° C., preferably at 0° C., for 2–24 h, at which time the reaction is quenched with aqueous, saturated sodium bicarbonate. Extractions with a suitable solvent, such as ethyl acetate, provide carbamate Va upon concentration. The carbamate and arylamine IIa are mixed in a non-protic, anhydrous solvent such as THF, ether, toluene, dioxane, methylene chloride or ethyl acetate. The preferred solvent is THF. The mixture is stirred at between 0–110° C., preferably at 0° C., for 2–48 h, in a sealed tube. PS-trisamine and PS-isocynate resins are added, and the reaction mixture was shaken for 3 days. Filtration and concentration provides the product of formula I (E=NH) or precursors thereof.

By using the appropriate starting material (G-EH), the above methods may also be used to prepare compounds of formula I with E=O or S.

Arylamine intermediates of formula IIa are either commercially available or can be made by methods known to those skilled in the art. Some of these methods are illustrated in the Synthetic Examples section.

Methods by which some intermediates III and IV, G'=Ar—X—Y—Z (Scheme I) may be prepared are described below, and also illustrated in the Synthetic Examples section. In Method E (Scheme II), a bromoarylamine VI, which may be commercially available or easily prepared by one skilled in the art, is reacted with a cycloalkenone VII in the presence of a transition metal catalyst, for example a palladium(II) catalyst such as bis(triphenylphosphine)palladium(II) chloride, in the presence of a bis(triphenylphosphine) chelator, such as 1,2- bis(diphenylphosphino)ethane (DPPE), 1,1'-bis(diphenylphosphino)ferrocene (DPPF) and 1,3-bis(diphenylphosphino)propane (DPPP), preferably DPPP, and a base, preferably sodium bicarbonate, in a suitable solvent, preferably DMF at a temperature of about 150° C. to provide VIII. VIII may then be used (as IV) in Method B (Scheme I), or converted to isocyanate IX by reaction with phosgene or a phosgene equivalent in the presence of a base, such as sodium bicarbonate in a suitable solvent such as dichloromethane, at a temperature of about 0° C., and used (as III) in Method A. The resulting product X may be modified further by methods known by one skilled in the art to obtain the desired compound of formula I.

In Method F, bromide XI is reacted with a strong base, such as t-butyl lithium, in a suitable solvent, such as THF, with tributyltin chloride at a temperature of about −50° C. to −100° C., preferably about −78° C. to give XII. XII is then reacted with VI in a suitable solvent, such as THF or 1,4-dioxane, in the presence of a transition metal catalyst, preferably tetrakis(triphenylphosphine)palladium(0), at a temperature of about 50° C. to 150° C., preferably about 100° C. and in a sealed tube, providing XIII. XIII may then be used (as IV) in Method B or C (Scheme I), or converted to the corresponding isocyanate as described in Method E, and used (as III) in Method A.

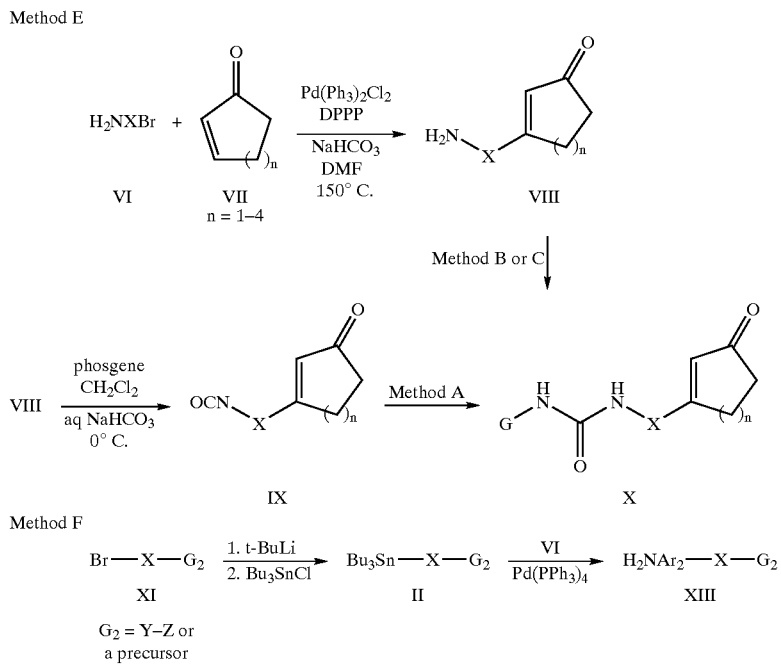

Methods by which Y and Z may be joined to X are known in the art, and two are illustrated in Scheme III. As illustrated by Method G, if one desires a product in which Y includes an amino nitrogen bonded to X, an X containing a ketone may be reacted with a Y-Z containing a terminal primary or secondary amine under reductive amination conditions. For example, ketone X is combined with a primary or secondary amine, in a suitable solvent such as THF. An acid, such as acetic acid, is added, followed by a suitable reducing agent, preferably sodium cyanoborohydride or sodium (triacetoxy) borohydride, to provide the desired product XIV.

Method H illustrates a procedure for obtaining a methylene group for Y and a primary or secondary amine for Z. An X group bearing an aldehyde and a halogen, preferably bromine (XV), may be reacted with a primary or secondary amine under reductive amination conditions as described in Method G to provide XVI. This intermediate may then be used as described for XI in Method F.

Scheme III

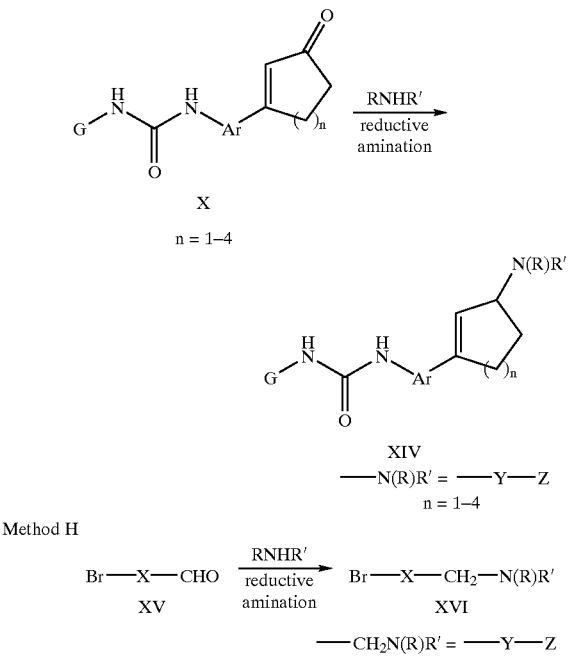

The synthesis of additional intermediates corresponding to IV and V may be accomplished by methods similar to those described in the literature or known to those skilled in the art. Some of these methods are exemplified in the synthetic examples below.

SYNTHETIC EXAMPLES

Intermediates IIa (G-NH$_2$, Scheme I) may be commercially available or prepared by methods known to those skilled in the art. Examples 1–3 provide representative procedures by which these intermediates may be synthesized.

Example 1

5-tert-Butyl-2-methoxy-3-nitroaniline

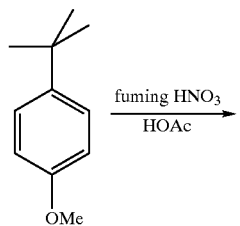

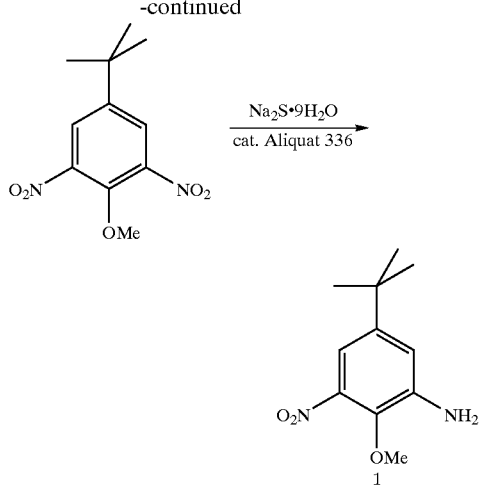

Fuming nitric acid (150 mL) was placed in a round bottom flask. A solution of 4-tert-butylanisole (16.4 g, 0.1 mol) in acetic acid (15 mL) was placed in an addition funnel and added dropwise to the flask. The flask was intermittently immersed in a water bath to maintain the temperature below 40° C. throughout the addition. Once the addition was complete, the reaction mixture was heated to 80° C., and maintained at that temperature for 2 h. The reaction mixture was cooled to ambient temperature, and then poured onto an ice/water mixture. A white solid soon formed, and the mixture was stirred for 30 min. The solid was isolated by vacuum filtration, and the filter cake was washed with water. The solid was dried on the filter. Recrystallization from hot 2-propanol provided 5-tert-butyl-2-methoxy-1,3-dinitrobenzene as white crystals (18.9 g, 75%).

To a suspension of 5-tert-butyl-2-methoxy-1,3-dinitrobenzene (10.2 g, 0.04 mol) in EtOAc (150 mL) was added in a single portion a solution of sodium sulfide nonahydrate (19.2 g, 0.08 mol) in water (200 mL). Aliquate® 336 (0.8 g, 5 mole %) was added in a single portion, and the two-phase mixture was brought to a reflux. All solids dissolved, and the mixture became red/brown. After about 3 h, TLC (3:1 hexanes:EtOAc) revealed almost complete loss of starting material. The mixture was filtered warm through a pad of diatomaceous earth to remove insolubles, and the filter cake was washed with fresh EtOAc. The clarified two-phase mixture was separated, and the organic layer was washed with sodium carbonate solution, followed by water and then saturated sodium chloride solution. After drying over magnesium sulfate, the solution was concentrated under reduced pressure to a thick, dark oil. This oil was extracted three times with refluxing hexanes, leaving behind a dark residue. The orange extract deposited some more dark oil, from which the warm supernatant was decanted. The resulting orange solution was heated back to reflux, and treated with both activated charcoal and diatomaceous earth. The solution was filtered hot, and the filter cake washed with hot hexanes. Re-heating the orange filtrate resulted in a clear solution. Quickly cooling the solution in an ice/acetone bath and scratching the flask with a glass rod resulted in the deposition of an orange/yellow precipitate. The suspension was allowed to cool for 1 h, and then filtered. The filter cake was washed with a small portion of cold hexanes, and then dried on the filter, providing the title compound as a yellow/orange powder (2.6 g, 30%).

Example 2

5-tert-Butyl-2-methoxy-3-methylcarbamoylaniline

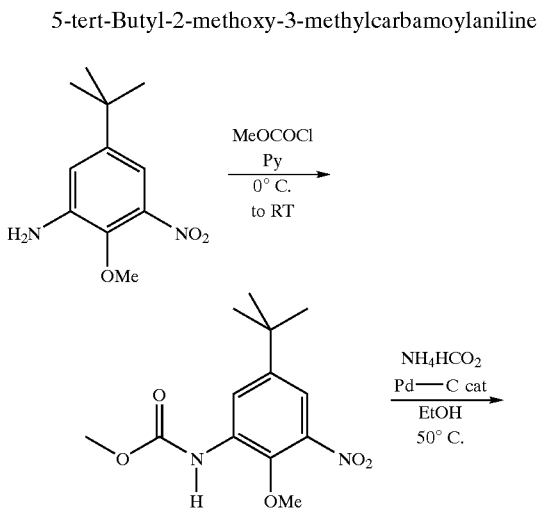

Example 3

N-(3-amino-5-tert-butyl-2-methoxyphenyl)-2-morpholin-4-yl-2-oxo-acetamide

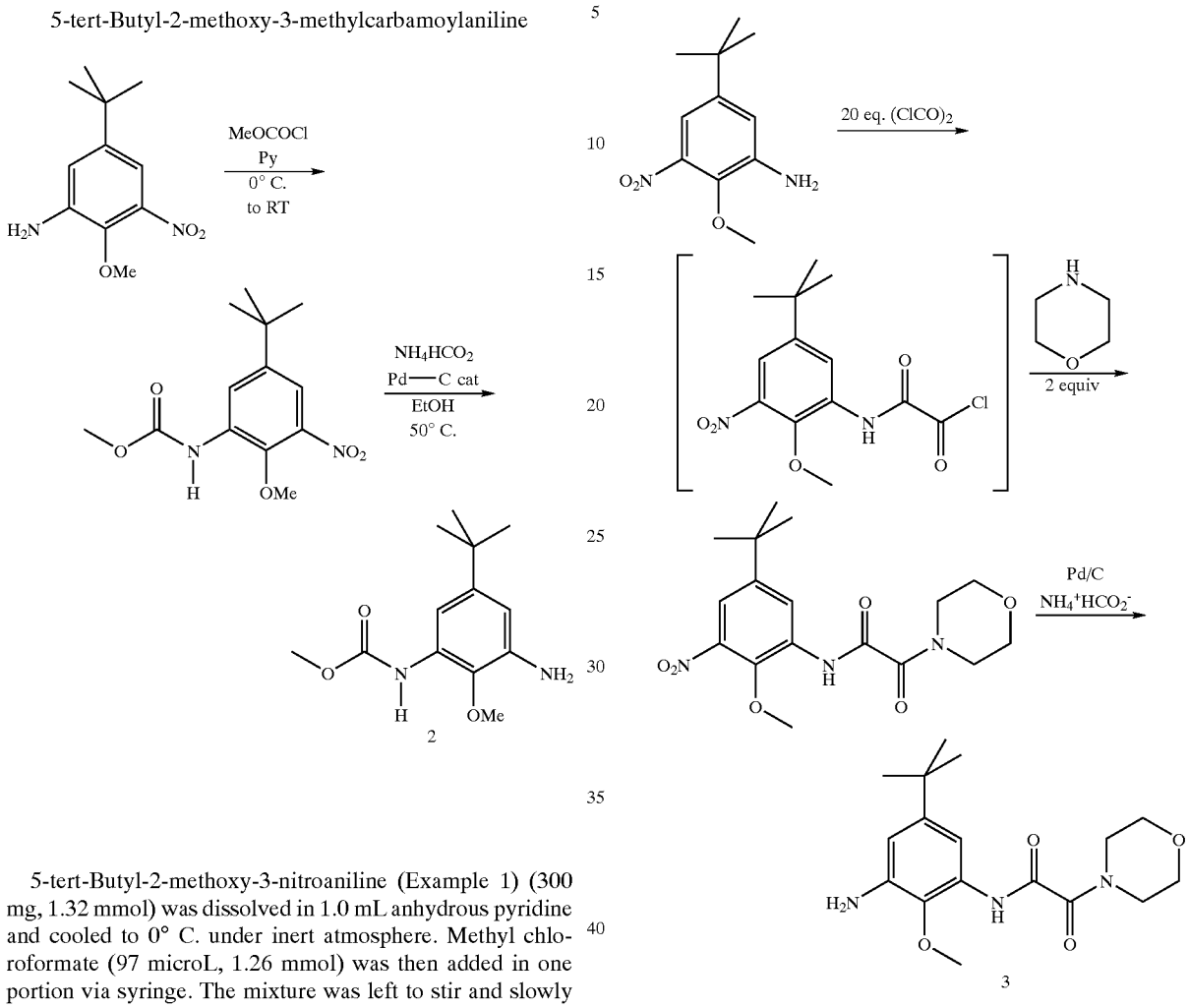

5-tert-Butyl-2-methoxy-3-nitroaniline (Example 1) (300 mg, 1.32 mmol) was dissolved in 1.0 mL anhydrous pyridine and cooled to 0° C. under inert atmosphere. Methyl chloroformate (97 microL, 1.26 mmol) was then added in one portion via syringe. The mixture was left to stir and slowly warm to room temperature overnight, then quenched with water (5 mL). The product was extracted with ether (3×5 mL) and dried over $Na_2SO_4$. The crude solution was filtered and the volatiles removed in vacuo. Purification by column chromatography on $SiO_2$ using 10–30% EtOAc in hexanes as eluent afforded 225 mg of the desired nitro-carbamate (0.80 mmol, 63% yield).

The above nitro-carbamate (225 mg, 0.80 mmol) dissolved in 5 mL EtOH was added to a solution of 10% palladium on carbon (225 mg) in 2 mL EtOH. Ammonium formate (301 mg, 4.8 mmol) was added and the mixture was heated to 50° C. for 1 h. The mixture was then cooled, filtered through a pad of diatomaceous earth, and the solvent removed in vacuo providing 200 mg (0.79 mmol, 99% yield) of the title compound.

The same general procedure outlined above may be used to prepare other desired alkyl or aryl carbamoyl anilines by substituting the appropriate alkyl or aryl chloroformate for methyl chloroformate.

Under a nitrogen purge, 5-tert-butyl-2-methoxy-3-nitroaniline (0.22 g, 0.001 mol) dissolved in 10 mL THF was added dropwise from an addition funnel into a solution of oxalyl chloride (1.7 mL, 0.02 mol) in 10 mL THF. The mild exotherm was controlled by slow addition rate. After the addition was complete, the reaction mixture was stirred 16 h at ambient temperature.

The THF and excess oxalyl chloride were removed under reduced pressure. Toluene was added to the residue and removed under reduced pressure two times to remove remaining traces of oxalyl chloride The resulting oil was dissolved in 15 mL THF under a nitrogen purge. A solution of morpholine (0.17 mL, 0.002 mol) in 15 mL THF was added dropwise from an addition funnel, causing an exotherm and a precipitate of morpholine hydrochloride. After the addition was complete, the suspension was allowed to stir 16 h at ambient temperature. The mixture was then briefly brought to reflux. The suspension was cooled to ambient, and solids removed by filtration. The solid was washed with fresh THF, and then the filtrate was concentrated in vacuo. The residue was partitioned between water and ether. The aqueous layer was washed twice with fresh ether, and the combined ether layers were washed with water and then with saturated NaCl solution. After drying over MgSO$_4$, solvent was removed to obtain the crude product as an oil. This material was purified by use of medium pressure chromatography on silica gel, eluting with a gradient of ethyl acetate in hexanes to provide N-(5-tert-butyl-2-methoxy-3-nitro-phenyl)-2-morpholin-4-yl-2-oxo-acetamide.

The above intermediate (0.18 g, 0.0005 mole) was dissolved in 15 mL CH$_3$CN under a nitrogen purge. In a single portion, ammonium formate (0.25 g, 0.004 mole) was added, followed by 10% palladium on carbon (0.05 g, 10 mole %). The resulting suspension was heated to reflux for two h. An aliquot indicated complete conversion of starting material. The reaction mixture was filtered hot through a pad of diatomaceous earth. The filter cake was washed twice with hot CH$_3$CN. Solvent was removed under reduced pressure to obtain an amber oil. This was partitioned between water and EtOAc. The aqueous layer was washed twice with fresh EtOAc, and the combined organic layer was washed first with water and then with saturated sodium chloride solution. After drying over MgSO$_4$, solvent was removed under reduced pressure. The resulting oil was purified by medium pressure chromatography on silica gel eluting with a gradient of 5 EtOAc:95 hexanes going to 30 EtOAc:70 hexanes) providing the title compound as a semi-solid.

The same general procedure outlined above may be used to prepare other desired oxo-acetamide intermediates by substituting the appropriate amine for morpholine. As would be known by one skilled in the art, one may use a suitable tertiary amine base such as triethylamine in place of excess amine being coupled.

Example 4

1-Amino-4-[5-(morpholin-4-ylmethyl)fur-2-yl]naphthalen-1-yl} urea

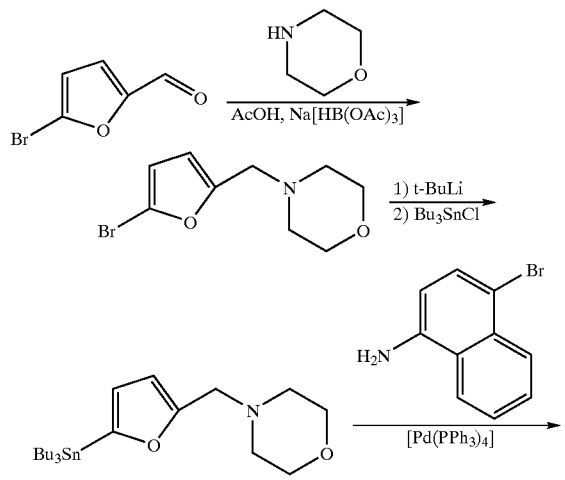

-continued

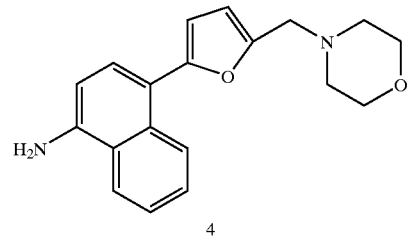

4

To a mixture of 5-bromo-2-furaldehyde (1.76 g) and morpholine (1.00 ml) in 40 mL anhydrous THF at room temperature was added acetic acid (0.60 mL) followed by sodium triacetoxyborohydride (3.28 g). The mixture was stirred at room temperature for 3 h and then poured into a saturated solution of sodium bicarbonate (100 mL). After stirring vigorously for 5 min the layers were separated and the aqueous layer was extracted with EtOAc. The combined organic layers were washed with brine, dried (Na$_2$SO$_4$), filtered and evaporated to dryness. Purification of the residue by flash chromatography afforded 2.09 g (8.49 mmol, 84% yield) of 4-(5-bromo-2-furylmethyl)morpholine.

The above intermediate (0.678 g, 2.76 mmol) was dissolved in 10 mL anhydrous THF under inert gas atmosphere and the solution was cooled to at −78° C. t-Butyllithium (4.0 mL of a 1.7 M solution in pentane) was added dropwise and the solution was stirred at −78° C. for 30 min. Tributyltinchloride (0.60 mL, 0.72 g, 2.2 mmol) was added and the solution was stirred for another 30 min at −78° C. pH7 Buffer (NaH$_2$PO$_4$/Na$_2$HPO$_4$ sat.) was added (10 mL) and the mixture was warmed to room temperature. The layers were separated and the aqueous layer was extracted with EtOAc. The combined organic layers were washed with brine, dried (Na$_2$SO$_4$), filtered and evaporated to dryness. Purification of the residue by flash chromatography afforded 0.526 g (1.15 mmol, 42% yield) of the tributylstannane intermediate.

The above intermediate (0.399 g, 0.874 mmol) and 1-amino-4-bromonaphthalene (0.200 g, 0.901 mmol) were dissolved in 10 mL anhydrous 1,4-dioxane in a sealable tube under inert gas atmosphere. The solution was degassed and purged with nitrogen (2×). Tetrakis(triphenylphosphine)palladium(0) (0.057 g, 0.049 mmol) was added and the solution was degassed and purged with nitrogen again (2×). The tube was sealed and heated to 100° C. for 24 h. After cooling to room temperature the mixture was diluted with EtOAc, saturated aqueous potassium carbonate solution (10 mL) was added and the mixture was stirred for 1 h at room temperature. The mixture was filtered over diatomaceous earth and the layers were separated. The aqueous layer was extracted with EtOAc. The combined organic layers were washed with brine, dried (Na$_2$SO$_4$), filtered an evaporated to dryness. Purification of the residue by flash chromatography afforded 0.314 g of a yellow oil, which contained the title compound along with tributyltin bromide. This mixture is suitable for use in Methods A-D without further purification.

Example 5

1-Amino-4-[3-(morpholin-4-yl)phenyl]naphthalene

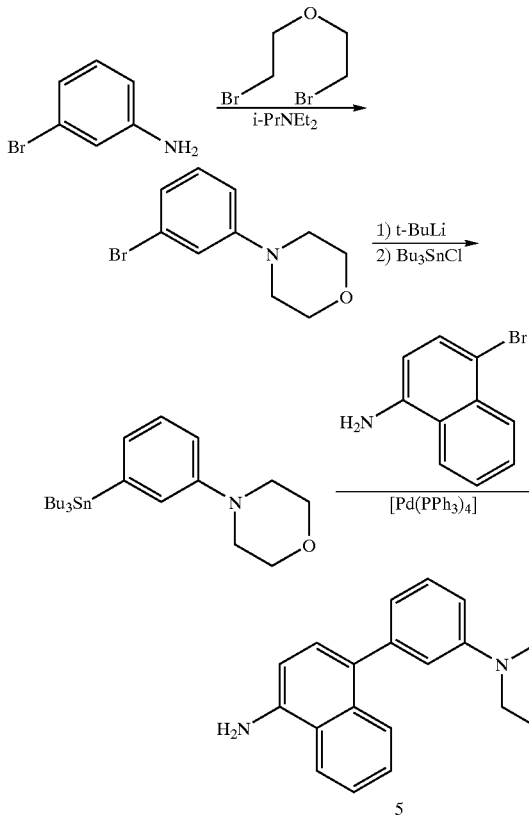

3-Bromoaniline (3.0 mL, 4.7 g, 28 mmol), 2-bromoethylether (4.2 mL, 7.7 g, 33 mmol) and diisopropylethylamine (15 mL, 11 g, 86 mmol) were dissolved in anhydrous DMF (20 mL) under inert gas atmosphere and heated to 100° C. for 6 h. After cooling to room temperature the mixture was poured into water (300 mL) and extracted with EtOAc. The combined organic layers were washed with brine, dried ($Na_2SO_4$), filtered and evaporated to dryness. Purification of the residue by flash chromatography afforded 2.9 g (12 mmol, 43% yield) of 4-(3-bromophenyl) morpholine.

4-(3-Bromophenyl)morpholine (1.73 g, 7.13 mmol) was dissolved in anhydrous THF (30 mL) and cooled to −78° C. t-Butyllithium (10.0 mL of a 1.7 M solution in pentane) was added dropwise and the solution was stirred at −78° C. for 30 min. Tributyltinchloride (1.90 mL, 2.28 g, 7.00 mmol) was added and the solution was stirred for another 45 min at −78° C. pH 7 Buffer ($NaH_2PO_4$/$Na_2HPO_4$ sat.) was added (10 mL) and the mixture was warmed to room temperature. The layers were separated and the aqueous layer was extracted with EtOAc. The combined organic layers were washed with brine, dried ($Na_2SO_4$), filtered an evaporated to dryness. Purification of the residue by flash chromatography afforded 2.28 g (5.36 mmol, 77% yield) of the tributylstannane intermediate.

The above intermediate (1.49 g, 3.51 mmol) and 1-amino-4-bromonaphthalene (0.69 g, 3.11 mmol) were dissolved in 20 mL anhydrous 1,4-dioxane in a sealable tube under inert gas atmosphere. The solution was degased and purged with nitrogen (2×). Tetrakis(triphenylphosphine)palladium(0) (0.21 g, 0.18 mmol) was added and the solution was degassed and purged with nitrogen again (2×). The tube was sealed and heated to 100° C. for 17 h. After cooling to room temperature the mixture was diluted with EtOAc, saturated aqueous potassium carbonate solution (10 mL) was added and the mixture was stirred for 1 h at room temperature. The mixture was filtered over diatomaceous earth and the layers were separated. The aqueous layer was extracted with EtOAc. The combined organic layers were washed with brine, dried ($Na_2SO_4$), filtered and evaporated to dryness. Purification of the residue by flash chromatography afforded 0.363 g (1.19 mmol, 38%) of title compound.

Example 6

5-(4-Aminonaphthalen-1-yl)-2-pyridin-3-ylmethylphenol

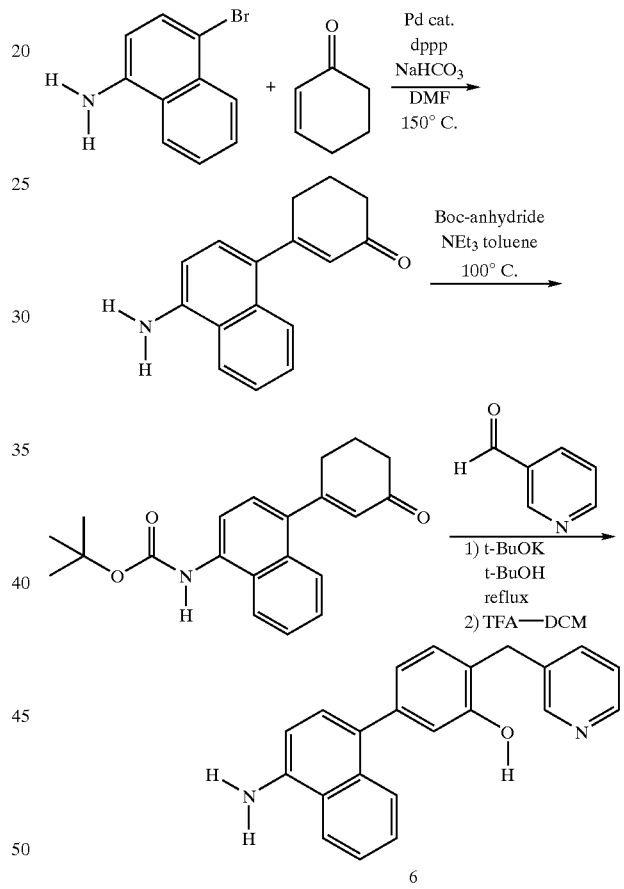

To a tube containing a solution of 2.0 g of 1-amino-4-bromonaphthalene (9.0 mmol, 1 equiv.) in 70 mL DMF were added 1.75 mL of 2-cyclohexen-1-one (18.0 mmol, 2.0 equiv.), 2.3 g of sodium bicarbonate (27.0 mmol, 3.0 equiv.) and 186 mg of 1,3-bis-(diphenylphosphino)propane (dppp, 0.45 mmol, 0.05 equiv.). A stream of dry nitrogen gas was bubbled through the mixture for 15 min, then 316 mg of bis-(triphenylphosphino)palladium(II) chloride (0.45 mmol, 0.05 equiv.) was added and the tube was sealed. The mixture was heated at 150° C. for 8 h, then cooled to ambient temperature, diluted with EtOAc (150 mL) and filtered through diatomaceous earth. The mixture was washed with water, then brine. The organic layer was dried ($MgSO_4$), filtered and concentrated. The crude oil was purified by column chromatography on SiO$_2$ using 10 to 50% EtOAc in hexane mixtures as eluents to give 2.0 g of a thick liquid consisting of 3-(4-aminonaphthalen-1-yl)cyclohex-2-enone and DMF (molar ratio 1:2 respectively, 5.22 mmol of naphthylamine, 58% of theoretical yield).

To a solution of 4.0 g of 3-(4-aminonaphthalen-1-yl)cycloxex-2-enone: DMF (1: 2, 10.4 mmol, 1 equiv.) in 50 mL toluene was added 2.72 g of di-tert-butyl dicarbonate (12.5 mmol, 1.2 equiv.) and 1.5 mL triethylamine (10.4 mmol, 1 equiv.). The mixture was heated to 100° C. overnight, then cooled to ambient temperature. The reaction mixture was washed with 0.1% aqueous HCl (2×50 mL), water, brine, dried (MgSO$_4$), filtered and concentrated. The crude product precipitated and was washed with 10% EtOAc in hexane to afford, after filtration, 2.5 g of desired tert-butyl carbamate (7.4 mmol, 71% of theoretical yield).

To a solution of 186 mg of the above tert-butyl carbamate (0.55 mmol, 1 equiv.) in 1.6 mL anhydrous tert-butanol was added 52 uL of pyridine-3-carboxaldehyde (0.55 mmol, 1 equiv.) and 1.65 mL potassium tert-butoxide solution (1.0 M, 1.32 mmol, 3 equiv.). The mixture was heated to reflux overnight, then cooled. MeOH (5 mL) and HCl solution in dioxane (4.0 M) were added until pH~1, the reaction was then stirred for 1.5 h at ambient temperature. The mixture was then quenched with saturated NaHCO$_3$ aqueous solution and extracted with EtOAc (2×50 mL). The aqueous layer was treated with 4 N NaOH aqueous solution until pH~12 and extracted 2 more times. The combined organic extracts were washed with brine, dried (MgSO$_4$), filtered and concentrated to afford a mixture of crude products, including naphthylamine still protected as the carbamate. The residue was therefore taken up in dichloromethane (3 mL), treated with 2 mL TFA and left stirring over a weekend at ambient temperature. The mixture was quenched and neutralized with saturated aqueous NaHCO$_3$, extracted with dichloromethane (3×50 mL), dried (MgSO$_4$) and filtered. The volatiles were removed in vacuo and the crude product purified by column chromatography on SiO$_2$ using 50 to 100% EtOAc in hexane eluent mixtures giving 35 mg (0.11 mmol, 20% of theoretical yield) title compound.

Example 7

5-(4-Aminonaphthalen-1-yl)-2-(tetrahydrofuran-3-ylmethyl)phenol

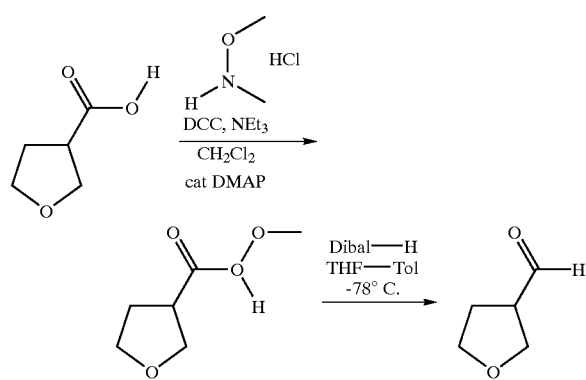

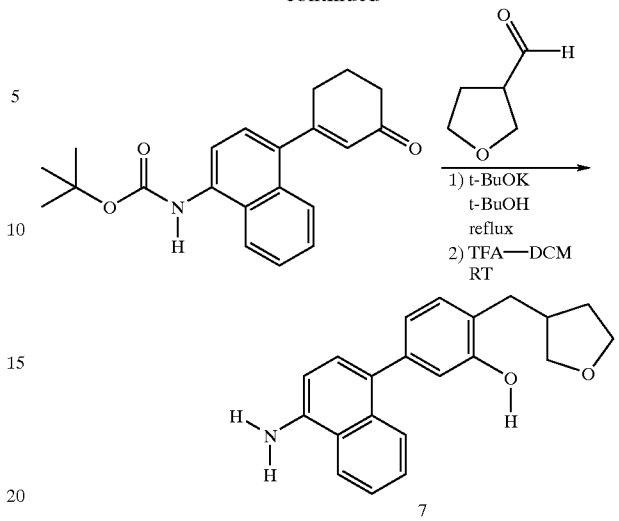

To a solution of 3.16 g of tetrahydro-3-furoic acid (27 mmol, 1 equiv.) in 25 mL anhydrous dichloromethane was added 7.85 g of dicyclohexylcarbodiimide (38 mmol, 1.4 equiv.) and 4.54 mL triethylamine (32.6 mmol, 1.2 equiv.). N-methyl-methanolamine hydrochloride was then added, followed by 60 mg of DMAP (4-dimethylamino)pyridine. An exothermic reaction ensued and a further 25 mL of dichloromethane were added. The mixture was stirred at ambient temperature overnight, then filtered through diatomaceous earth and concentrated. The residue was treated with ether and the white solid filtered off and removed. The solvent was removed from the mother liquor and the residue purified by column chromatography on SiO$_2$ using 15–25% EtOAc in hexanes as eluent mixtures to provide the desired amide as a colorless oil (55% of theoretical yield) that still contained 10% of dicyclohexyl urea. This was used without further purification in the next reaction.

To a solution of 1.0 g of the above amide (6.28 mmol, 1 equiv.) in 60 mL anhydrous THF at −78° C. was added 12.6 mL of 1.0 M DIBAL-H solution in toluene dropwise via syringe (12.6 mmol, 2.0 equiv.). After stirring 30 min at −78° C. the reaction mixture was quenched with 50 mL MeOH and 50 mL water. The reaction mixture was transferred to a separatory funnel and 250 mL ether were added. 1 N HCl aqueous solution was added until all the solids had dissolved. The layers were separated and the aqueous portion was extracted further with 2×100 mL ether. The combined organics were washed with saturated aqueous NaHCO$_3$ solution, then brine, dried over Na$_2$SO$_4$, filtered and concentrated. The crude product was purified by chromatography on silica gel using 0–5% MeOH in dichloromethane as eluent mixtures. The desired 3-tetrahydrofuroic aldehyde was obtained as a very volatile, impure colorless oil (200 mg).

To a solution of 200 mg of tert-butyl naphthyl carbamate (Example 6) (0.59 mmol, 1 equiv.) in 1.6 mL anhydrous tert-butanol was added 200 mg of 3-tetrahydrofuroic aldehyde from above (excess) and 1.78 mL potassium tert-butoxide solution in tert-butanol (1.0 M, 1.78 mmol, 3 equiv.). The mixture was heated to 40° C. overnight, then cooled and quenched with NH$_4$Cl saturated aqueous solution. The product was extracted with a dichloromethane/MeOH mixture (3×100 mL). The combined extracts were washed with brine, dried over MgSO$_4$, and concentrated. $^1$H NMR analysis revealed that only 10% of the enone was consumed. The residue (300 mg) was dissolved in 4.0 mL dichloromethane and treated with 4 mL of a 1:1 mixture dichloromethane: TFA. The mixture was stirred for 1.5 h, then neutralized with saturated $NaHCO_3$ aqueous solution, basified with 4 N NaOH solution and extracted with dichloromethane/MeOH (3×100 mL). The combined organic extracts were washed with brine, dried ($MgSO_4$) and filtered and concentrated. The crude product was purified by column chromatography on silica gel using 10 to 50% EtOAc in hexane eluent mixtures to give the title compound (35 mg 0.11 mmol, 19% of theoretical yield).

Example 8

4-[5-(4-Aminonaphthalen-1-yl)pyridin-2-yloxy]butyronitrile

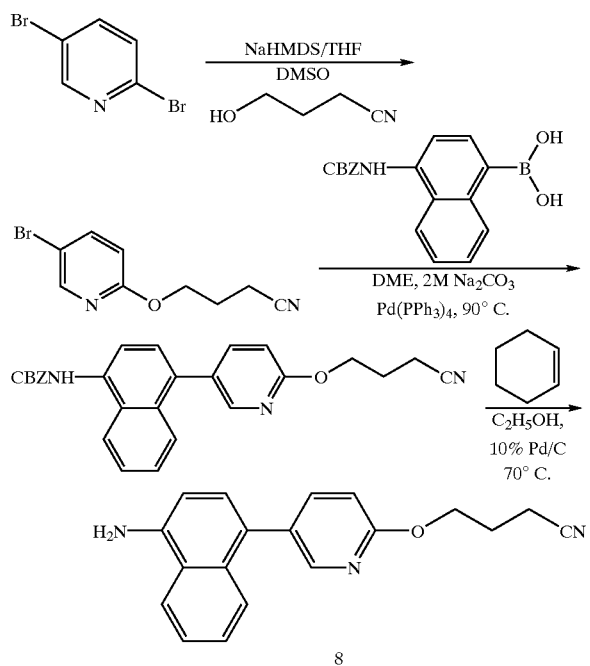

8

To 2,5-dibromopyridine (500 mg, 2.1 mmol) and 3-cyano-1-propanol (270 mg, 3.1 mmol) in DMSO (2 mL) was added IM sodium hexamethyldisilazide (2.1 mL, 2.1 mmol). The reaction was stirred at room temperature overnight. EtOAc was added to the reaction and the mixture was washed with water (2×10 mL). The EtOAc fraction was dried over anhydrous sodium sulfate and evaporated on a rotary evaporator. The crude product was purified by flash column chromatography over silica gel using 40%EtOAc/hexanes to give 200 mg of 5-bromo-2-cyanopropyloxypyridine as a pale yellow solid (39.3%).

To the above intermediate (100 mg, 0.4 mmol) and CBZ-protected naphthylboronic acid (prepared as described for the Boc-analog Example 12) (200 mg, 0.62 mmol) in DME (4 mL) was added 2M sodium carbonate solution (2 mL). The solution was purged with nitrogen for 10 min and to this was added palladium tetrakistriphenylphosphine (20 mg). The reaction was heated at 90° C. for 48 h and then cooled to room temperature. EtOAc was added to the reaction and the mixture was washed with water (2×10 mL). The EtOAc fraction was dried over anhydrous sodium sulfate, filtered and concentrated. The crude product was purified by flash column chromatography over silica gel eluting with 40%EtOAc/hexanes to give 70 mg of the desired coupled intermediate (39%).

To the above coupled intermediate (70 mg, 0.16 mmol) in EtOH (5 mL) was added cyclohexene (263 mg, 3.2 mmol) and 10%Pd/C (20 mg). The reaction was heated under nitrogen overnight and cooled to room temperature. The reaction was filtered over diatomaceous earth, washed with MeOH and concentrated. The crude product was purified by flash column chromatography over silica gel eluting with 50% EtOAc/hexanes to give 15 mg of the title compound (31%).

Example 9

[5-(4-Aminonaphthalen-1-yl)pyridin-2-yl]-(tetrahydrothiopyran-4-yl) amine dihydrochloride

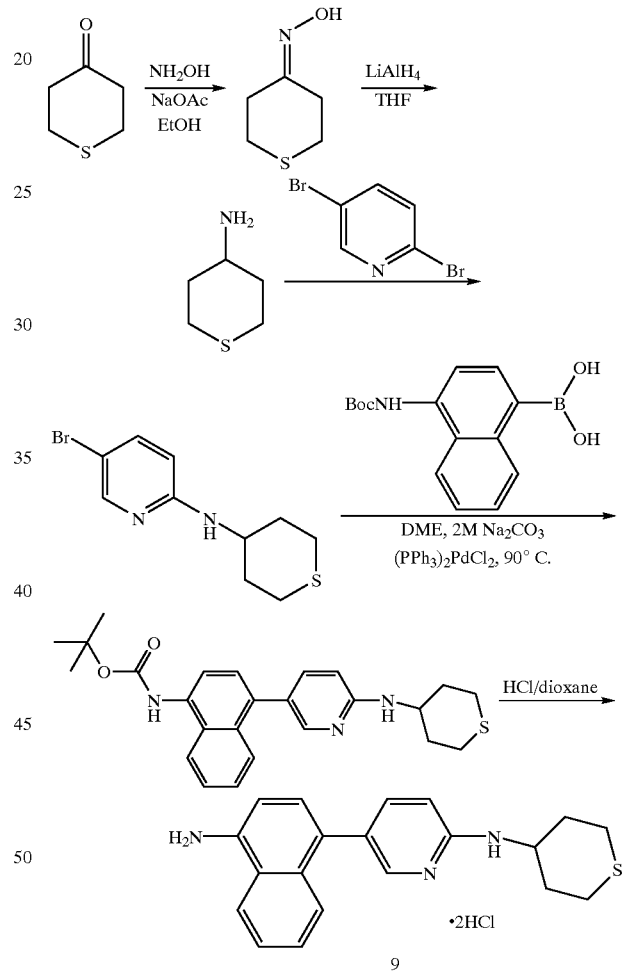

9

To tetrahydro-1,4-thiopyrone (2.0 g, 17.2 mmol) and hydroxylamine hydrochloride (2.0 g, 28.7 mmol) in EtOH (10 mL) was added sodium acetate trihydrate (4.0 g, 29.4 mmol) in 20 mL water. The reaction was heated at reflux for 3 h, cooled to room temperature and concentrated to 15 mL on a rotary evaporator. The residue was cooled in an ice-bath and filtered to give 2.0 g of the oxime product as a white solid m.p. 80–83° C. (88.7%).

To a dry flask containing THF (20 mL) and IM lithium aluminium hydride in diethyl ether (19 mL) at room temperature, was added the oxime from above (500 mg, 3.82 mmol). The reaction was heated at reflux for 3 h, cooled to room temperature and the excess LAH was quenched with ice/water. Extraction with EtOAc and concentration gave 340 mg (76%) of the desired 4-aminotetrahydrothiopyran.

To the above amine (170 mg, 1.4 mmol) in dry pyridine (1 mL) was added 2,5-dibromopyridine (250 mg, 1.1 mmol) and the reaction was heated at 110–120° C. for 5 days. The reaction was extracted with EtOAc, washed with water, dried over anhydrous sodium sulfate and concentrated to give the crude product. The crude product was purified by flash column chromatography over silica gel using 30% EtOAc/hexanes as eluent to give 100 mg of pure product (33.3%).

To the above intermediate (80 mg, 0.293 mmol) and BOC-protected naphthylboronic acid (See Example 12) (140 mg, 0.488 mmol) in DME (4 mL) was added 2 M sodium carbonate (2 mL) and bis(triphenylphosphine) palladium chloride (15 mg). The reaction was heated at 90° C. under nitrogen for 18 h and cooled to room temperature. The reaction was extracted with EtOAc, washed with water, dried over anhydrous sodium sulfate and concentrated to give the crude product. The crude product was purified by flash column chromatography over silica gel using 30% EtOAc/hexanes as eluent to give 110 mg of the coupled intermediate (86.0%)

To the coupled intermediate (35 mg, 0.08 mmol) in dioxane (1 mL) was added 4 M HCl/dioxane (0.6 mL). The reaction was stirred at room temperature for 48 h. Addition of diethyl ether gave the product as the hydrochloride salt which was filtered, giving 18 mg (55%) of the title compound.

Example 10

[5-(4-Aminonaphthalen-1-yl)pyridin-2-yl]-(tetrahydropyran-4-yl) amine dihydrochloride

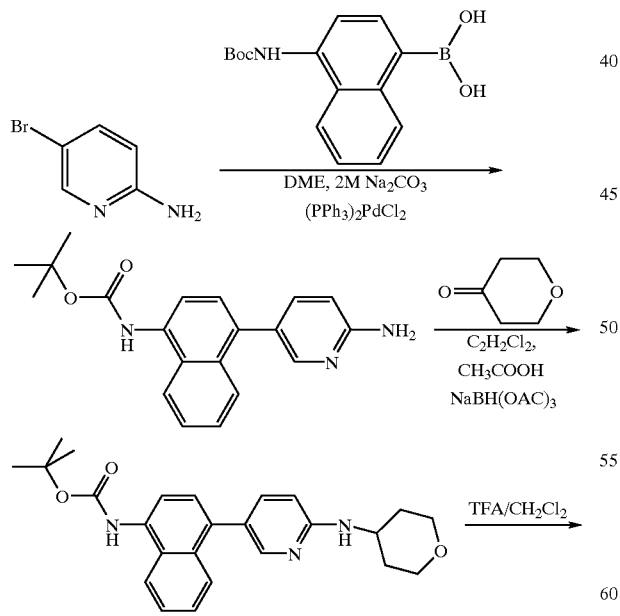

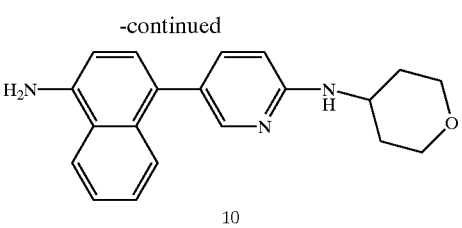

10

To 2-amino-5-bromopyridine (250 mg, 1.44 mmol) and BOC-protected naphthylboronic acid (see Example 12) (688 mg, 2.4 mmol) in 5 mL DME was added 2 M sodium carbonate (2.5 mL) and bis(triphenylphosphine)palladium chloride (30 mg). The reaction was heated at 90° C. under nitrogen for 18 h and cooled to room temperature. The reaction mixture was extracted with EtOAc, washed with water, dried over anhydrous sodium sulfate and concentrated. The residue was purified by flash column chromatography over silica gel eluting with 40% EtOAc/hexanes to give 370 mg coupled intermediate (76.4%).

To the above intermediate (200 mg, 0.597 mmol) and tetrahydropyranone (120 mg, 1.19 mmol) in dichloroethane (5 mL) was added glacial acetic acid (0.2 mL, 3.58 mmol) and sodium triacetoxyborohydride (380 mg, 1.79 mmol). The reaction was stirred at room temperature for 48 h and then extracted with EtOAc, washed with water, dried over anhydrous sodium sulfate and concentrated. The residue was purified by flash column chromatography over silica gel using 50% EtOAc/hexanes as eluent to give 120 mg Boc-protected title compound (48.0%).

The Boc-protected title compound was dissolved in dichloromethane (3 mL) and treated with trifluoroacetic acid (1 mL). The reaction was stirred for 3 h and concentrated. The residue was dissolved in EtOAc (20 mL), washed with sodium bicarbonate solution, dried over anhydrous sodium sulfate concentrated to give 90 mg of the title compound 17 (98.5%).

Example 11

[5-(4-Aminonaphthalen-1-yl)pyridin-2-yl]-(1-methylpiperidin-4-yl) amine

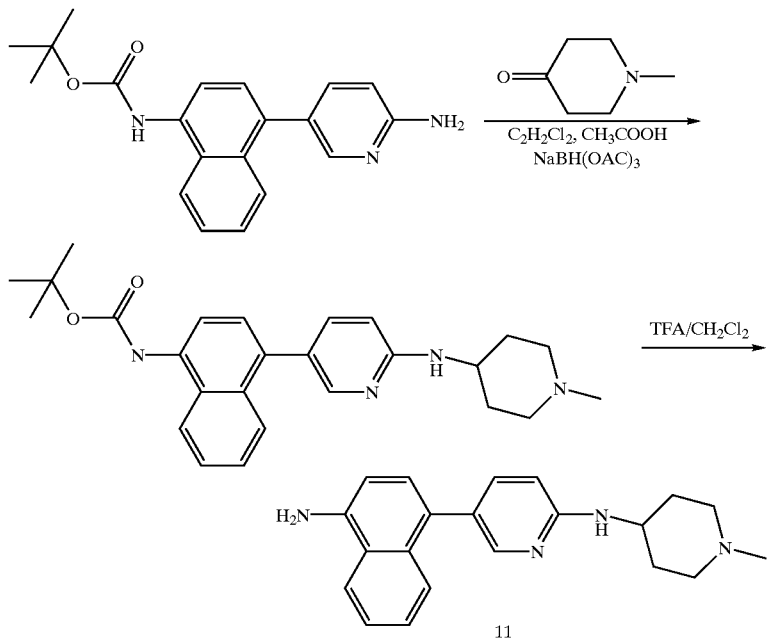

To a mixture of 5-(4-N-Boc-aminonaphthyl)pyridin-2-ylamine (Example 10) (110 mg, 0.33 mmol) and 1-methyl-4-piperidone (80 mg, 0.7 mmol) in dichloroethane (6 mL) was added glacial acetic acid (120 mg, 2.0 mmol) and sodium triacetoxyborohydride (220 mg, 1.03 mmol). The reaction was stirred at room temperature for 96 h and then extracted with EtOAc, washed with water, dried over anhydrous sodium sulfate and concentrated. The residue was purified by flash column chromatography over silica gel using 10%MeOH/CH$_2$Cl$_2$/0.1% TEA as eluent to give 60 mg of the N-Boc-derivative of the title compound (42%).

The above intermediate was dissolved in dichloromethane (3 mL) and treated with trifluoroacetic acid (1 mL). The reaction was stirred for 2.5 h and then concentrated to give 94 mg of the title compound (100%).

Example 12

4-[5-(Aminonaphthyl)pyridin-2-ylmethyl]morpholine

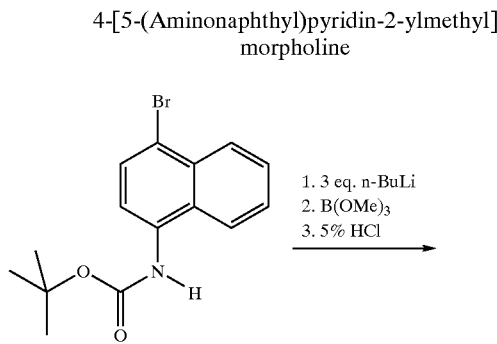

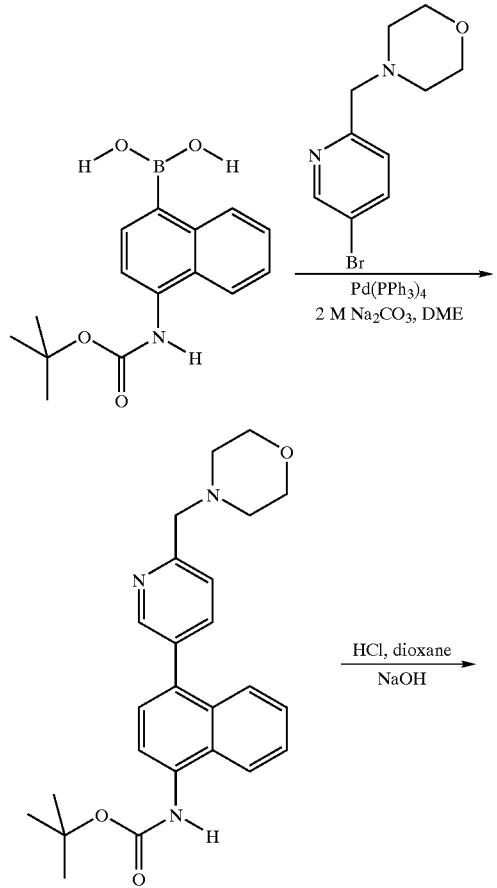

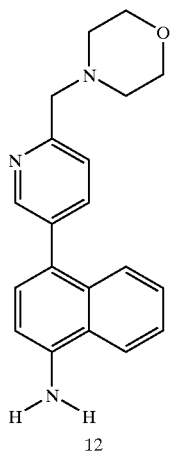

To a stirred solution of N-Boc-1-amino-4-bromo naphthalene (15.5 mmol) in anhydrous THF (40 mL) at −78° C. was added n-BuLi (47 mmol). The resultant yellow-green solution was stirred at −78° C. for two h then was transferred to a solution of trimethylborate (5.64 grams, 54.2 mmol) in anhydrous THF (25 mL) at 42° C. The reaction was allowed to warm to room temperature overnight as the bath warmed. After stirring for 16 h, 5% aqueous HCl was added (25 mL) and the mixture was stirred for 15 min. The aqueous layer was saturated with NaCl and the layers were separated. The aqueous portion was extracted with diethyl ether (3×60 mL) and the combined organics were extracted with 0.5 M NaOH (6×30 mL). The combined basic extracts were acidified to pH ~2 with 3 M HCl (~30 mL) and the suspension was extracted with diethyl ether (3×100 mL). The combined ethereal extracts were dried ($MgSO_4$), filtered and the solvent was removed to afford the boronic acid as a beige solid (2.3 g) which was used without further purification.

This boronic acid (0.70 mmol) and 5-bromo-2-(morpholin-4-ylmethyl)pyridine (0.70 mmol) were dissolved in a biphasic mixture of dimethoxyethane (2 mL) and 2 M aq. $Na_2CO_3$ (1 mL). The reaction was purged with a stream of $N_2$ for 15 min, the Pd catalyst was added, and the mixture was heated at 85° C. for 16 h. The reaction was cooled to room temperature and was partitioned between water (10 mL) and EtOAc (75 mL). The layers were separated and the organic portion was washed with brine (20 mL), dried ($MgSO_4$), filtered and the solvent was removed to afford a brown solid. Column chromatography afforded the product as a beige solid.

This material (0.50 mmol) was dissolved in 2 mL anhydrous dioxane and HCl was added (2.5 mmol). The solution was stirred at room temperature for 16 h. To the resultant suspension was added diethyl ether (5 mL) and the mixture was chilled to 0° C. Neutralization with aq. NaOH and filtration afforded the title compound as a light brown solid (100 mg).

The following are representative examples of methods in Scheme I for preparing compounds of formula I Example 13

1-[4-(6-Morpholin-4-ylmethyl-pyridin-3-yl)-naphthalen-1-yl]-3-[5-tert-butyl-3-(2-methoxyethylcarbamoyl)-2-methoxyphenyl]-urea

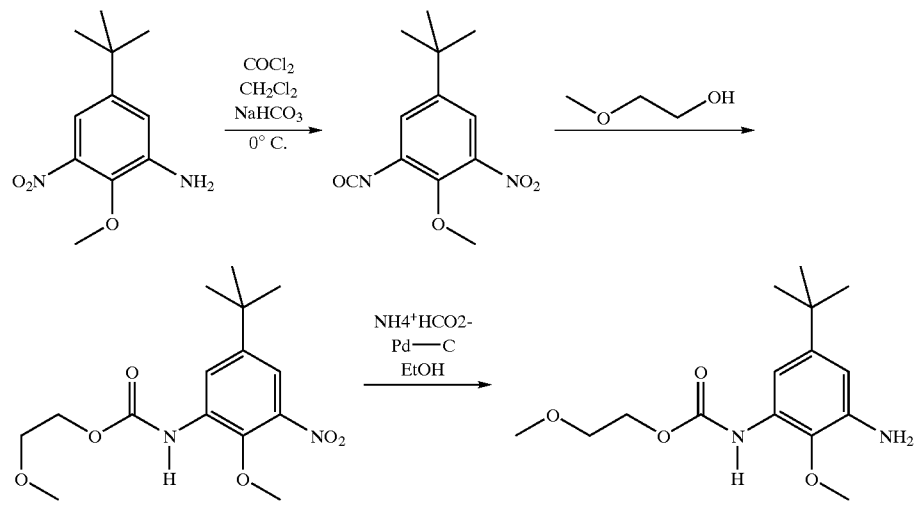

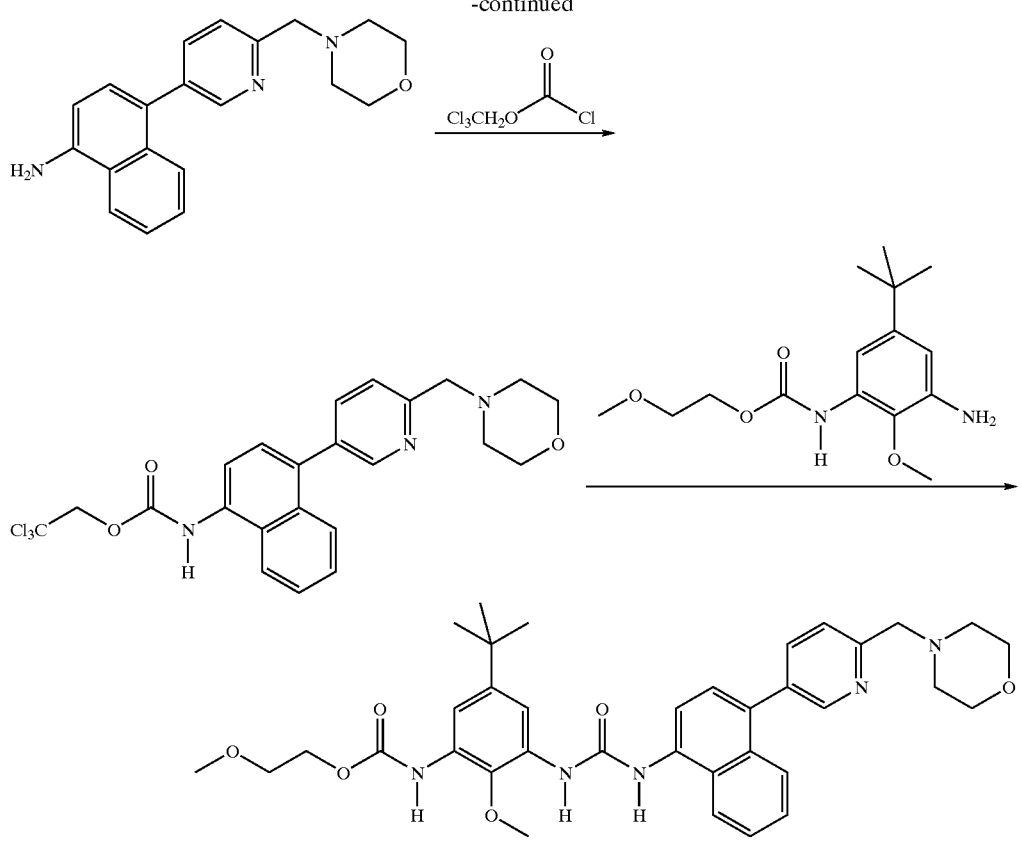

13

5-tert-Butyl-2-methoxy-3-nitroaniline (Example 1) (1.20 g, 5.3 mmol, 1 equiv.) was dissolved in 100 mL anhydrous dichloromethane. An equal volume of a saturated, aqueous NaHCO$_3$ solution was added and the mixture was cooled to 0° C., while vigorously stirring. After 20 min stirring was stopped, and a solution of phosgene (~2 M in toluene, 10.6 mL, 21.3 mmol, 4 equiv.) was added in one portion via syringe to the organic layer. Stirring was resumed and after 30 min at 0° C., the mixture was transferred to a separatory funnel. The aqueous layer was separated and extracted once with dichloromethane (50 mL). The combined organics were dried over Na$_2$SO$_4$, the solution was filtered and the volatiles removed in vacuo. The corresponding isocyanate was obtained and was used in the next step without purification.

The next steps were run on a parallel synthesizer, using the above isocyanate and a variety of commercially available alcohols. The sequence of steps is exemplified for the derivative resulting from reaction with 2-methoxyethanol. The sequence described may also be run in a non-parallel fashion in conventional glassware.

2-Methoxyethanol (79 uL, 1.0 mmol, 1.2 equiv.) in 2.0 mL anh. THF was treated with a solution of the above isocyanate (0.833 mmol, 1 equiv.) in THF and the mixture was stirred under nitrogen overnight. The solvent was then removed in vacuo and the product was purified by flash chromatography on SiO$_2$ eluting with 0–25% EtOAc in hexanes. 5-tert-Butyl-2-methoxy-3-(2-methoxyethylcarbamoyl)-1-nitrobenzene was thus obtained (90 mg, 0.28 mmol, 33% yield).

The above nitrobenzene (90 mg, 0.28 mmol, 1 equiv.) was dissolved in 5 mL absolute EtOH and placed in a 10 mL reaction vessel. Ammonium formate (104 mg, 1.64 mmol, 6 equiv.) and palladium-on-carbon (10%, 90 mg) were added and the mixture was heated to 50° C. under nitrogen. Heating and stirring were continued for 1 h, then allowed to cool and the reaction was filtered. The reaction vessel was rinsed with 3×2 mL MeOH. Supernatant and washings were combined in a vial and the solvents were removed in a vacuum centrifuge oven. The corresponding aniline was thus obtained (82 mg, 0.28 mmol, 100% yield) and was used without purification.

4-[5-(4-Aminonaphthyl)pyridin-2-ylmethyl]morpholine (Example 12) (788 mg, 2.46 mmol, 1 equiv.) in 8 mL anh. THF at 0° C. was treated with 2,2,2-trichloroethyl chloroformate (0.36 mL, 2.59 mmol, 1.05 equiv.) and the mixture was stirred and allowed to slowly warm to room temperature overnight. The mixture was then quenched with saturated aqueous NaHCO$_3$ and the product extracted with EtOAc (3×50 mL). The combined organic extracts were washed with water, then brine. They were then dried (MgSO$_4$), filtered, and the solvents were removed in vacuo. The trichloroethyl carbamate was thus obtained as a light pink solid (1.24 g, 2.50 mmol, quant. yield) and was used without purification.

The trichloroethyl carbamate (147 mg, 0.28 mmol, 1 equiv.) and diisopropylethylamine (0.14 mL, 0.78 mmol, 2.8 equiv.) were added to the aniline intermediate from above (82 mg, 0.28 mmol, 1 equiv.) in 1.0 ml anh. DMSO. The mixture was stirred and heated to 75° C. overnight. The mixture was then cooled, filtered and the reaction vessel rinsed with EtOAc. Volatiles were removed in a vacuum centrifuge oven overnight and the residue was purified using

Example 14

(5-tert-Butyl-2-methoxy-3-{3-[4-(6-morpholin-4-ylmethyl-pyridin-3-yl)-naphthalen-1yl]ureido}-phenyl)-carbamic acid 2-morpholin-4-yl-ethyl ester

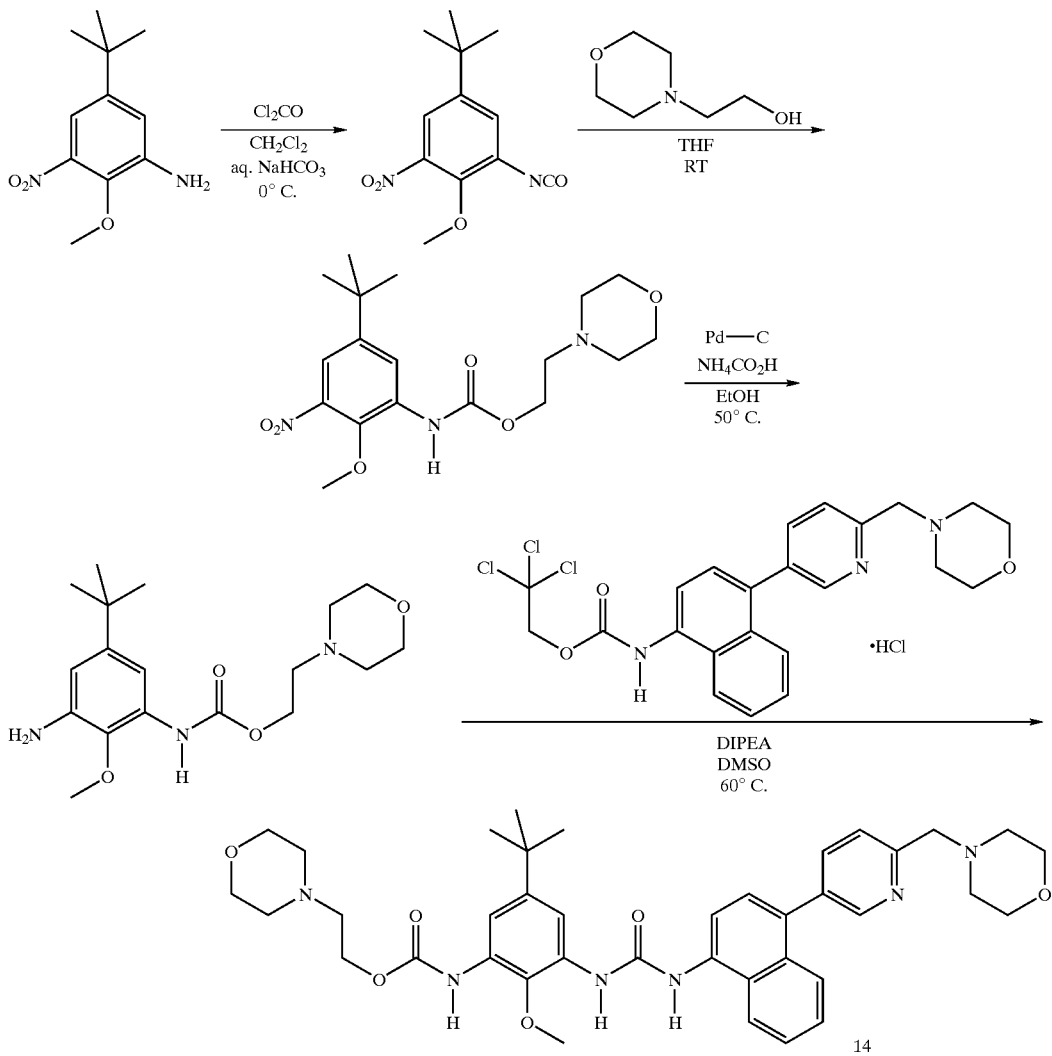

5-tert-Butyl-2-methoxy-3-nitroaniline (Example 1) (1.2 g, 5.3 mmol, 1 equiv.) was dissolved in 100 mL methylene chloride and 100 mL of a saturated solution of NaHCO₃ was added. The mixture was cooled in an ice bath, and without stirring the mixture, phosgene (~2 M in toluene, 10.6 ml, 21.3 mmol, 4.0 equiv.) was added via syringe in one portion to the organic layer. The reaction mixture was vigorously stirred for 30 min at 0° C., then it was transferred to a separatory funnel, and the organic layer was collected and dried over Na₂SO₄. The solution of isocyanate was concentrated in vacuo and used as is in the next step.

4-(2-Hydroxyethyl)-morpholine (0.120 mL, 1.0 mmol, 1.2 equiv.) dissolved in 2.0 mL anhydrous THF was added to a solution of the above isocyanate (0.833 mmol, 1 equiv.) in 1.0 mL THF and the mixture was stirred at room temperature overnight. The solvent was then removed in vacuo and the residue purified by column chromatography on SiO₂ using 0–25% EtOAc in hexanes eluent mixtures providing the desired nitrophenyl carbamate (250 mg, 0.656 mmol, 78% yield).

The above carbamate (250 mg, 0.656 mmol, 1 equiv.) was dissolved in 5 mL absolute EtOH and transferred to a 10 mL reaction vessel. Ammonium formate (248 mg, 6 equiv.) and palladium-on-carbon (10% w/w, 250 mg) were added and the mixture was heated to 50° C. under inert atmosphere. After one h heating was stopped and the vessel was allowed to cool. The mixture was filtered, the supernatant being collected in a vial. The reaction vessel was rinsed 3 times with 2 mL MeOH, the washings being collected in the vial. The vial was placed in a vacuum centrifuge oven to remove the solvent. The resulting aniline (218 mg, 95% yield) was used in the subsequent step without purification.

The above aniline (115 mg, 0.326 mmol, 1 equiv.) was placed in a 10 mL reaction vessel and was dissolved in 0.75 mL anhydrous DMSO. The trichloroethyl carbamate hydrochloride intermediate (173 mg, 0.326 mmol, 1 equiv.) and diisopropylethylamine (0.160 mL, 0.913 mmol, 2.8 equiv.) were added. DMSO (0.25 mL) was used to wash down all reagents and ensure proper mixing. The reaction vessel was heated at 75° C. for 6 h, then cooled to room temperature. Using a little EtOAc, the contents of the reaction vessel were then transferred to a vial and placed in a vacuum centrifuge oven to remove all solvents. The title compound (53 mg) was obtained pure after preparative HPLC.

Example 15

(5-tert-Butyl-2-methoxy-3-{3-[4-(6-morpholin-4-ylmethyl-pyridin-3-yl)-naphthalen-1-yl]-ureido}-phenyl)-carbamic acid isopropyl ester of the above isocyanate (0.833 mmol, 1 equiv.) in 1.0 mL THF and the mixture was stirred at room temperature overnight. The solvent was then removed in vacuo and the residue purified by column chromatography on $SiO_2$ using 0–15% EtOAc in hexanes eluent mixtures providing the desired nitrophenyl carbamate (220 mg, 0.710 mmol, 85% yield).

The above carbamate (220 mg, 0.710 mmol, 1 equiv.) was dissolved in 5 mL absolute EtOH and transferred to a 10 mL reaction vessel. Ammonium formate (269 mg, 6 equiv.) and palladium-on-carbon (10% w/w, 220 mg) were added and

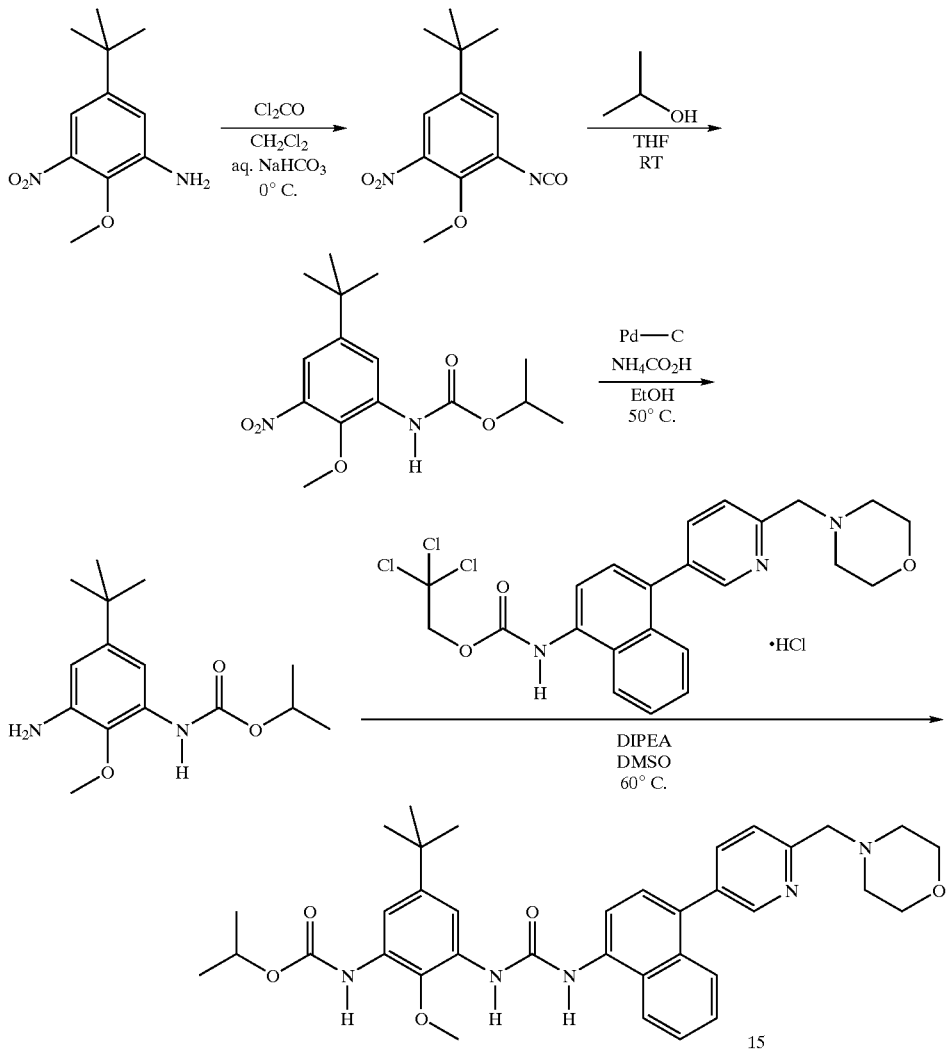

5-tert-Butyl-2-methoxy-3-nitroaniline (Example 1) (1.2 g, 5.3 mmol, 1 equiv.) was dissolved in 100 mL methylene chloride and 100 mL of a saturated solution of $NaHCO_3$ was added. The mixture was cooled in an ice bath, and without stirring the mixture, phosgene (~2 M in toluene, 10.6 ml, 21.3 mmol, 4.0 equiv.) was added via syringe in one portion to the organic layer. The reaction mixture was vigorously stirred for 30 min at 0° C., then it was transferred to a separatory funnel, and the organic layer was collected and dried over $Na_2SO_4$. The solution of isocyanate was concentrated in vacuo and used as is in the next step.

Isopropyl alcohol (0.077 mL, 1.0 mmol, 1.2 equiv.) dissolved in 2.0 mL anhydrous THF was added to a solution the mixture was heated to 50° C. under inert atmosphere. After one h heating was stopped and the vessel was allowed to cool. The mixture was filtered, the supernatant being collected in a vial. The reaction vessel was rinsed 3 times with 2 mL MeOH, the washings being collected in the vial. The vial was placed in a vacuum centrifuge oven to remove the solvent. The resulting aniline (189 mg, 95% yield) was used in the subsequent step without purification.

The above aniline (82 mg, 0.343 mmol, 1.2 equiv.) was placed in a 10 mL reaction vessel and was dissolved in 0.75 mL anhydrous DMSO. The trichloroethyl carbamate hydrochloride intermediate (150 mg, 0.285 mmol, 1 equiv.) and diisopropylethylamine (0.139 mL, 0.798 mmol, 2.8 equiv.)

were added. DMSO (0.25 mL) was used to wash down all reagents and ensure proper mixing. The reaction vessel was heated at 75° C. for 6 h, then cooled to room temperature. Using a little EtOAc, the contents of the reaction vessel were then transferred to a vial and placed in a vacuum centrifuge oven to remove. all solvents. The title compound (29 mg) was obtained pure after preparative HPLC.

Example 16

(5-tert-Butyl-2-methoxy-3-{3-[4-(6-morpholin-4-ylmethyl-pyridin-3-yl)-naphthalen-1-yl]-ureido}-phenyl)-carbamic acid methyl ester 4-[5-(Aminonaphthyl)pyridin-2-ylmethyl]morpholine (Example 12) (223.7 mg, 0.70 mmol, 1 equiv.) was dissolved in 30 mL dichloromethane and stirred with a saturated aqueous solution of NaHCO$_3$ while cooling to 0° C. for 20 min. Stirring was stopped and phosgene (~2.0 M in tolune, 1.4 mL, 2.8 mmol, 4.0 equiv.) was added to the organic layer in one portion via syringe. Stirring was resumed, vigorously, for 20 min. The mixture was then transferred to a separatory funnel and the organic layer was collected, dried (Na$_2$SO$_4$) and filtered. Most of the solvents (except toluene) were then removed in vacuo to afford a dark yellow solution that was used without purification in the next step.

To the naphthyl-isocyanate solution from above was added the 5-tert-butyl-2-methoxy-3-methylcarbamoylaniline (200 mg, 0.79 mmol, 1.1 equiv.) in 5.0 mL anhydrous THF, under inert atmosphere. The mixture was left stirring overnight, then the solvent was removed in vacuo. The crude product was purified by column chromatography on SiO$_2$ to afford 304 mg of a foam (72% yield). This purified material was recrystallized from ether/CH$_3$CN mixtures to afford a white solid, which was

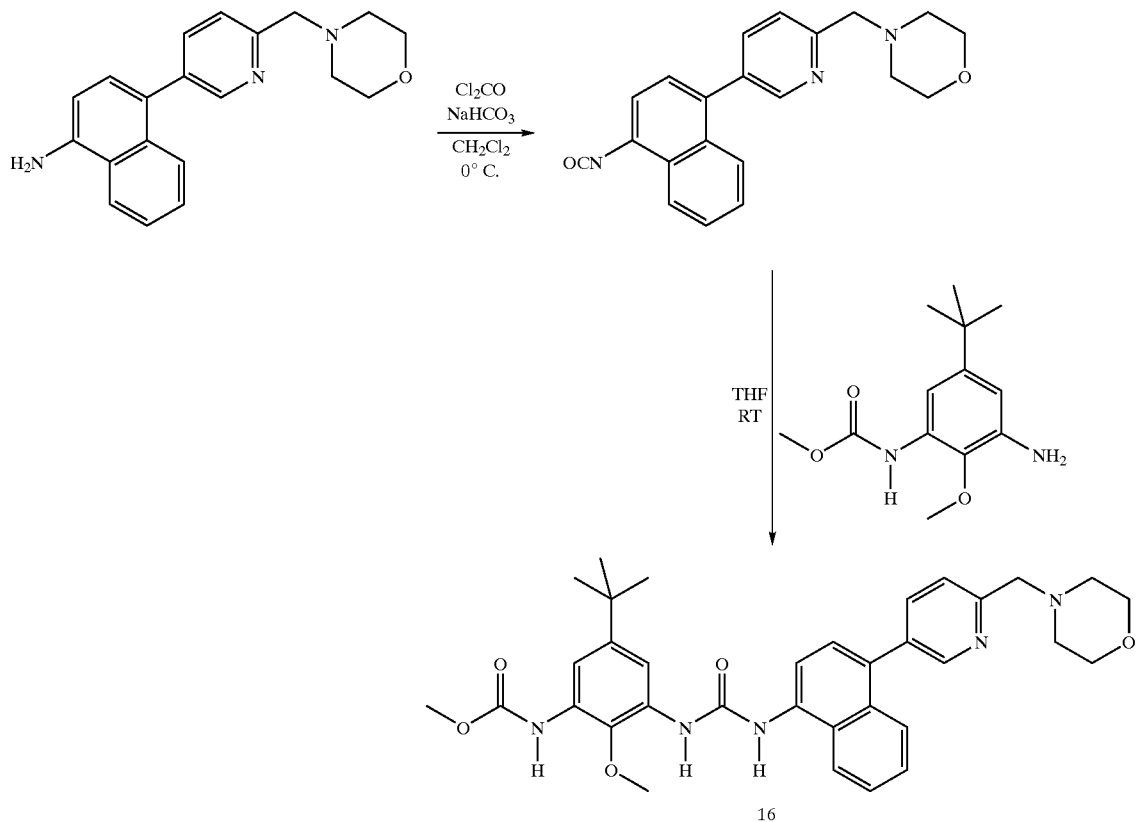

dried under high vacuum at 60° C. until no ether was present by $^1$H NMR, providing 179 mg title compound, mp 192–193° C.

Example 17

N-(5-tert-Butyl-2-methoxy-3-{3-[4-(6-morpholin-4-ylmethyl-pyridin-3-yl)-naphthalen-1-yl]-ureido}-phenyl)-2-morpholin-4-yl-2-oxo-acetamide

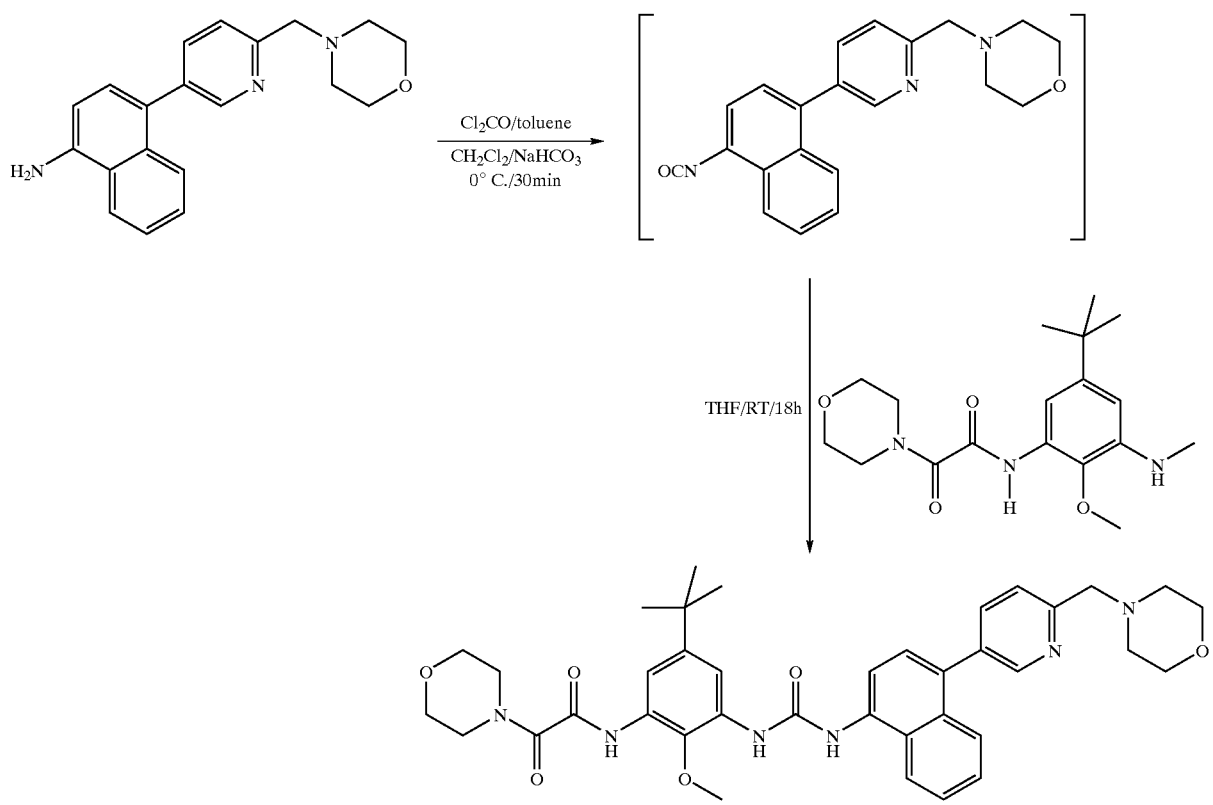

4-[5-(Aminonaphthyl)pyridin-2-ylmethyl]morpholine (Example 12) (0.1 g, 0.0003 mol) was dissolved in methylene chloride (10 mL), and the solution was cooled to −5° C. in an ice/acetone bath under a nitrogen purge. A saturated sodium bicarbonate solution (10 mL) was added in a single portion. Phosgene (0.5 mL of a 20% solution in toluene) was added to an addition funnel, along with 3 mL of methylene chloride. This solution was added dropwise to the rapidly stirring two-phase reaction mixture over 15 min, causing a slight exotherm and a yellow color. Stirring was continued another 30 min, whereupon the lower organic phase was separated. The aqueous layer was washed twice with fresh portions of methylene chloride, and the combined organic layer was dried with magnesium sulfate. Volatiles were removed in vacuo (maintaining the bath temperature below 35° C.), to provide a solution of the isocyanate in toluene. N-(3-amino-5-tert-butyl-2-methoxy-phenyl)-2-morpholin-4-yl-2-oxo-acetamide (Example 3) (0.1 g, 0.0003 mol) was dissolved in THF (10 mL). The isocyanate/toluene solution from above was placed in an addition funnel, along with 5 mL THF. Under a nitrogen purge, this solution was added dropwise to the reaction mixture. The reaction was stirred 18 h at ambient temperature. Volatiles were removed in vacuo and the residue was partitioned between water and EtOAc. The aqueous layer was washed twice with fresh EtOAc, and the combined organic layer was washed with saturated sodium chloride, and then dried over magnesium sulfate. Solvent was removed in vacuo, and the residue was purified by chromatography (silica gel column, elution with a gradient of MeOH in methylene chloride). Appropriate fractions were combined, and solvent was removed in vacuo to provide the title compound.

Assessment of Biological Properties

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP. 1 cells ($2\times10^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/ml final; Siga L-2630, from *E.coli* serotype 0111.B4; stored as 1 mg/ml stock in endotoxin screened distilled $H_2O$ at −80° C.). Blanks (unstimulated) received $H_2O$ vehicle; final incubation volume was 250 µl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds including those from the synthetic examples above were evaluated and had $IC_{50}$<10 uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1, G M-CSF, IL-6 and IL-8 can be demonstrated (for example, see J. C. Lee et al., 1988, *Int. J. Immunopharmacol.*, 10, 835).

What is claimed is:

1. A compound of the formula (I):

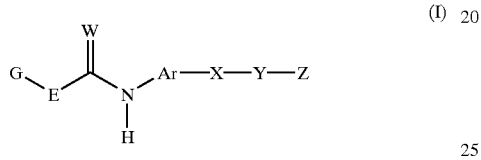

wherein:
E is
is a group chosen from —O—, —NH— and —S—;
G is:
phenyl, naphthyl, benzocyclobutanyl, dihydronaphthyl, tetrahydronaphthyl, benzocycloheptanyl, benzocycloheptenyl, indanyl, indenyl;
pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzooxazolyl, benzofuranyl, benzothiophenyl, benzpyrazolyl, dihydrobenzofuranyl, dibenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, 2,3-dihydro-1H-indolyl, indolinyl, indolonyl, indolinonyl, phthalimidyl, chromoyl;
oxetanyl, pyrrolidinyl, tetrahydrofuranyl, tetrahydrothiophenyl, piperidinyl, piperazinyl, morpholino, tetrahydropyranyl, dioxanyl, tetramethylene sulfonyl, tetramethylene sulfoxidyl, oxazolinyl, 3,4-dihydro-2H-benzo[1,4]oxazinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholino, thiazolidinyl, dihydrooxazinyl, dihydropyranyl, oxocanyl, heptacanyl, thioxanyl or dithianyl;
wherein G is substituted by one $R_3$ and further substituted by one or more $R_1$ or $R_2$;
Ar is:
phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:
a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;
aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperidinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino) carbonyl, $NH_2C(O)$, $C_{1-6}$ alkyl-$S(O)_m$ or halogen;
Y is:
a bond or a $C_{1-10}$ saturated or unsaturated branched or unbranched carbon chain, wherein one or more C atoms are optionally replaced by O, N, or $S(O)_m$; and wherein Y is optionally partially or fully halogenated and optionally independently substituted with one to two oxo groups, nitrile, amino, imino, phenyl or one or more $C_{1-4}$ alkyl optionally substituted by one or more halogen atoms;
Z is:
morpholinyl, optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl) amino; or Z is optionally substituted with one to three amino or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy; or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;
each $R_1$ is independently:
$C_{1-10}$ alkyl branched or unbranched optionally partially or fully halogenated, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl,
or $R_1$ is
cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, nitrile, hydroxy$C_{1-3}$alkyl or aryl;
phenyloxy or benzyloxy each being optionally partially or fully halogenated and optionally substituted with one to three $C_{1-3}$ alkyl groups optionally partially or fully halogenated, nitrile, hydroxy$C_{1-3}$alkyl or aryl;

cyclopropyl, cyclobutyl, cyclopentyl, cyclohexyl, cycloheptyl, bicyclopentanyl, bicyclohexanyl or bicycloheptanyl, each being optionally partially or fully halogenated and optionally substituted with one to three $C_{1-3}$ alkyl optionally partially or fully halogenated, nitrile, hydroxy$C_{1-3}$alkyl or aryl;

$C_{3-10}$ branched or unbranced alkenyl each being optionally partially or fully halogenated, and optionally substituted with one to three $C_{1-5}$ branched or unbranched alkyl, phenyl, naphthyl, cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

oxo, nitrile, halogen; or $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, one or more $C_{1-4}$ alkyl optionally substituted by one or more halogen atoms, nitrile, morpholinyl, piperidinyl, piperazinyl, imidazolyl, phenyl, pyridinyl, tetrazolyl, or mono- or di($C_{1-3}$alkyl) amino optionally substituted by one or more halogen atoms;

each $R_2$, $R_4$, and $R_5$ is a $C_{1-6}$ branched or unbranched alkyl optionally partially or fully halogenated, $C_{1-6}$acyl, aroyl, $C_{1-4}$ branched or unbranched alkoxy, each being optionally partially or fully halogenated, halogen, methoxycarbonyl, $C_{1-4}$ alkyl-$S(O)_m$ branched or unbranched and optionally partially or fully halogenated, or phenyl-$S(O)_m$;

$R_3$ which is covalently attached to G, is

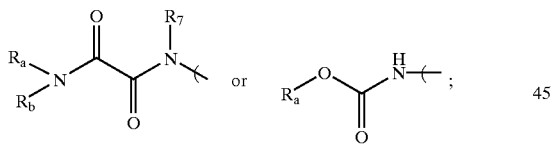

wherein for $R_3$:

$R_a$ and $R_b$ are each independently: hydrogen, a $C_{1-10}$ saturated or unsaturated branched or unbranched carbon chain, wherein one of the C atoms is optionally replaced by O or N and optionally substituted by oxo;

or $R_a$ and $R_b$ are each independently $C_{3-7}$ cycloalkyl$C_{0-6}$ alkyl, phenyl$C_{0-6}$ alkyl, heterocycle$C_{0-6}$ alkyl or heteroaryl$C_{0-6}$ alkyl wherein the $C_{0-6}$ alkyl portion for each is optionally substituted by oxo and wherein the heterocycle or heteroaryl moiety is chosen from morpholinyl, pyridinyl, piperidinyl, piperazinyl, pyrimidinyl, pyrazinyl, pyridazinyl, pyrrolyl, pyrrolidinyl, imidazolyl, pyrazolyl, thiazolyl, oxazolyl, oxazoyl,[1,3,4]oxadiazol, triazolyl, tetrazolyl, isoxazolyl, isothiazolyl, quinolinyl, isoquinolinyl, indolyl, benzimidazolyl, benzoxazolyl, benzisoxazolyl, benzpyrazolyl, quinoxalinyl, quinazolinyl and indazolyl, each $C_{3-7}$ cycloalkyl, phenyl, heterocycle or heteroaryl is optionally substituted by $C_{1-6}$ alkyl, halogen, hydroxy, carboxy, oxo, amino, imino, nitro or nitrile;

or $R_a$ and $R_b$ together with the nitrogen atom to which they are attached form a morpholino, pyridinyl, piperidinyl, piperazinyl, pyrimidinyl, pyrazinyl, pyridazinyl, pyrrolyl, pyrrolidinyl, imidazolyl, pyrazolyl, thiazolyl, oxazolyl, oxazoyl, [1,3,4]oxadiazol, triazolyl, tetrazolyl, isoxazolyl, isothiazolyl, quinolinyl, isoquinolinyl, indolyl, benzimidazolyl, benzoxazolyl, benzisoxazolyl, benzpyrazolyl, cinnolinyl, pterindinyl, phthalazinyl, naphthypyridinyl, quinoxalinyl, quinazolinyl, purinyl or indazolyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl and cyclohexanoimidazolyl, wherein each of the above is optionally substituted by one to three $R_6$, wherein $R_6$ is chosen from oxo, halogen, nitro, hydroxy, carboxy nitrile, amino, imino, guanidino, phenyl or $C_{1-4}$ alkyl optionally substituted by one or more halogen atoms; $R_7$ is hydrogen or $C_{1-6}$ branched or unbranched alkyl optionally partially or fully halogenated;

m is 0, 1, 2 or 3 and

W is O or S or the pharmaceutically acceptable salts, acids, esters or isomers thereof.

2. The compound according to claim 1 wherein:

$R_3$ is

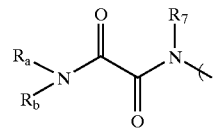

$R_7$ is hydrogen;

E is —NH—; and

W is O.

3. The compound according to claim 2 wherein:

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperidinyl, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino) carbonyl, $NH_2C(O)$, $C_{1-6}$ alkyl-$S(O)_m$ or halogen; and Z is optionally substituted with one to three nitrile, $C_{1-3}$ alkyl, $C_{1-3}$ alkoxy, amino, mono- or di-($C_{1-3}$ alkyl)amino, $CONH_2$ or OH; or Z is optionally substituted by phenyl morpholinyl each in turn is optionally substituted by halogen, $C_{1-3}$ alkyl or $C_{1-3}$ alkoxy.

4. The compound according to claim 3 wherein:

G is
  phenyl, pyridinyl, pyridonyl, naphthyl, quinolinyl, isoquinolinyl, pyrazinyl, benzothiophenyl, dihydrobenzofuranyl, dihydrobenzothiophenyl, benzooxazolyl, indanyl, indolyl, indolinyl, indolonyl or indolinonyl, wherein G is substituted by one $R_3$ and further substituted by one or more $R_1$ or $R_2$;

Ar is naphthyl;

X is
  phenyl, imidazolyl, pyridinyl, pyrimidinyl, piperidinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:
  a bond or
  a $C_{1-4}$ saturated carbon chain wherein one or more of the C atoms is optionally replaced by O, N or S and wherein Y is optionally independently substituted with nitrile or oxo;

Z is optionally substituted with one to two $C_{1-2}$ alkyl or $C_{1-2}$ alkoxy;

each $R_1$ is independently:
  $C_{1-5}$ alkyl branched or unbranched optionally partially or fully halogenated, wherein one or more C atoms are optionally independently replaced by O, N or $S(O)_m$, and wherein said $C_{1-5}$ alkyl is optionally substituted with oxo,
  cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; oxo;
  $C_{2-4}$ alkynyl optionally partially or fully halogenated wherein one or more methylene groups are optionally replaced by O, and optionally independently substituted with one to two oxo groups, hydroxy, $C_{1-4}$ alkyl optionally substituted by one or more halogen atoms, nitrile, or mono- or di-($C_{1-3}$alkyl) amino optionally substituted by one or more halogen atoms; and each $R_2$ is independently:
  a $C_{1-4}$ alkyl optionally partially or fully halogenated, $C_{1-4}$ alkoxy optionally partially or fully halogenated, bromo, chloro, fluoro, methoxycarbonyl, methyl-$S(O)_m$, ethyl-$S(O)_m$ each optionally partially or fully halogenated or phenyl-$S(O)_m$.

5. The compound according to claim 4 wherein:

G is:
  phenyl, pyridinyl, pyridonyl, 2-naphthyl, quinolinyl, isoquinolinyl, dihydrobenzofuranyl, indanyl, 5-indolyl, indolinyl, indolonyl, or indolinonyl, wherein G is substituted by one $R_3$ and further substituted by one or more $R_1$ or $R_2$;

Ar is 1-naphthyl;

X is:
  phenyl, imidazolyl, pyridinyl, pyrimidinyl, piperidinyl, piperazinyl, pyridazinyl or pyrazinyl and wherein X is attached to the 4-position of Ar;

Y is:
  a bond or
  —$CH_2$—, —$CH_2CH_2$—, O—$CH_2CH_2$—, —C(O)—, —O—, —S—, —NH—$CH_2CH_2$—, —N($CH_3$)—, $CH_2(CN)CH_2$—NH—$CH_2$ or —NH—;

Z is:
  morpholinyl;

$R_1$ is:
  $C_{1-5}$ alkyl optionally partially or fully halogenated wherein one or more C atoms are optionally independently replaced by O or N, and wherein said $C_{1-5}$ alkyl is optionally substituted with oxo;
  cyclopropyl, cyclopentanyl, cyclohexanyl and bicyclopentanyl optionally substituted with one to three methyl groups optionally partially or fully halogenated, nitrile, hydroxymethyl or phenyl;

$R_2$ is:
  $C_{1-4}$ alkoxy optionally partially or fully halogenated, bromo, chloro, fluoro, nitrile, nitro, amino; and
  $R_a$ and $R_b$ are each independently hydrogen, $C_{1-5}$ alkyl, phenyl$C_{0-5}$ alkyl optionally substituted on the phenyl by $C_{1-6}$ alkyl, halogen, hydroxy, carboxy, oxo, amino, imino, nitro or nitrile;
  or $R_a$ and $R_b$ together with the nitrogen atom to which they are attached form a morpholinyl, piperidinyl, piperazinyl, pyridinyl, pyrimidinyl, pyrazinyl, pyridazinyl, pyrrolyl, pyrrolidinyl, imidazolyl, pyrazolyl, oxazolyl, isoxazolyl and isothiazolyl, each optionally substituted by one to two $R_6$.

6. The compound according to claim 5, wherein:

G is:
  phenyl or pyridinyl wherein G is substituted by one $R_3$ and further substituted by one or more $R_1$ or $R_2$;

X is:
  phenyl, imidazolyl, pyridinyl, pyrimidinyl or pyrazinyl;

Y is:
  a bond, —$OCH_2CH_2$—, —$CH_2CH_2$—, —O—, $CH_2(CN)CH_2$—NH—$CH_2$, —$CH_2$—, —NH—$CH_2CH_2$— or —NH—;

Z is:
  morpholin-4yl;

$R_1$ is:
  tert-butyl, sec-butyl, phenyl, or cyclohexanyl;
  $R_a$ and $R_b$ are each independently hydrogen, a $C_{1-4}$ alkyl, phenyl, benzyl wherein the phenyl or phenyl portion of the benzyl are optionally substituted by methyl, halogen, hydroxy, carboxy, amino;
  or $R_a$ and $R_b$ together with the nitrogen atom to which they are attached form a morpholinyl, piperidinyl, piperazinyl or pyrrolidinyl, each optionally substituted by one to two $R_6$;
  and $R_6$ is $C_{1-4}$ alkyl, halogen, nitro, nitrile, hydroxy, carboxy or oxo.

7. The compound according to claim 6 wherein

G is phenyl substituted by $R_3$ and one to two $R_1$ or $R_2$;

X is phenyl or pyridin-3yl;

$R_a$ and $R_b$ are each independently hydrogen, a $C_{1-3}$ alkyl, phenyl or benzyl;

or $R_a$ and $R_b$ together with the nitrogen atom to which they are attached form a morpholinyl, piperidinyl, piperazinyl or pyrrolidinyl, each optionally substituted by one to two $R_6$; and $R_6$ is $C_{1-3}$ alkyl or halogen;

Y is:
a bond, —OCH$_2$CH$_2$—, —CH$_2$CH$_2$—, —O—, —CH$_2$—, —NH—CH$_2$CH$_2$— or —NH—.

8. The compound according to claim 7 wherein:
the attachment of X to Ar and Y is at the following X positions: 3-,6-pyridinyl or 1-,4-phenyl, respectively;
Y is —CH$_2$— and
$R_6$ is methyl or ethyl.

9. The compound according to claim 1 wherein:
$R_3$ is:

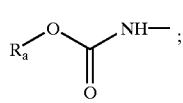

E is —NH— and
W is O.

10. The compound according to claim 9 wherein:
Ar is:
naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperidinyl, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino)carbonyl, NH$_2$C(O), $C_{1-6}$ alkyl-S(O)$_m$ or halogen;

Z is: morpholinyl optionally substituted with one to three nitrile, $C_{1-3}$ alkyl, $C_{1-3}$ alkoxy, amino, mono- or di-($C_{1-3}$ alkyl)amino, CONH$_2$ or OH;
or Z is optionally substituted by phenyl, heterocycle or heteroaryl as hereinabove described in this paragraph each in turn is optionally substituted by halogen, $C_{1-3}$ alkyl or $C_{1-3}$ alkoxy; and $R_a$ is a $C_{1-10}$ saturated or unsaturated branched or unbranched carbon chain, wherein one of the C atoms is optionally replaced by O or N and optionally substituted by oxo;
or $R_a$ is $C_{3-7}$ cycloalkyl$C_{0-6}$ alkyl, phenyl$C_{0-6}$ alkyl, heterocycle$C_{0-6}$ alkyl or heteroaryl$C_{0-6}$ alkyl wherein the $C_{0-6}$ alkyl portion is optionally substituted by oxo and wherein the heterocycle or heteroaryl moiety is chosen from morpholinyl, pyridinyl, piperidinyl, piperazinyl, pyrimidinyl, pyrazinyl, pyridazinyl, pyrrolyl, pyrrolidinyl, imidazolyl, pyrazolyl, thiazolyl, oxazolyl, oxazoyl, [1,3,4]oxadiazol, triazolyl, tetrazolyl, isoxazolyl and isothiazolyl, each $C_{3-7}$ cycloalkyl, phenyl, heterocycle or heteroaryl is optionally substituted by $C_{1-6}$ alkyl, halogen, hydroxy, carboxy, oxo, amino, nitro or nitrile.

11. The compound according to claim 10 wherein:
G is
phenyl, pyridinyl, pyridonyl, naphthyl, quinolinyl, isoquinolinyl, pyrazinyl, 3,4-dihydro-2H-benzo[1,4]oxazinyl, benzothiophenyl, dihydrobenzofuranyl, dihydrobenzothiophenyl, benzooxazolyl, indanyl, indolyl, indolinyl, indolonyl or indolinonyl, wherein G is substituted by one $R_3$ and further substituted by one or more $R_1$ or $R_2$;

Ar is naphthyl;

X is
phenyl, imidazolyl, pyridinyl, pyrimidinyl, piperidinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, NH$_2$C(O), $C_{1-6}$ alkyl-S(O)$_m$ or halogen;

Y is:
a bond or
a $C_{1-4}$ saturated carbon chain wherein one or more of the C atoms is optionally replaced by O, N or S and wherein Y is optionally independently substituted with nitrile or oxo;

Z is:
morpholinyl optionally substituted with one to two $C_{1-2}$ alkyl or $C_{1-2}$ alkoxy;

each $R_1$ is independently:
$C_{1-5}$ alkyl branched or unbranched optionally partially or fully halogenated, wherein one or more C atoms are optionally independently replaced by O, N or S(O)$_m$, and wherein said $C_{1-5}$ alkyl is optionally substituted with oxo, dioxolanyl, pyrrolidinyl, furyl or phenyl each optionally substituted with one to three halogen, $C_{1-3}$ alkyl which is optionally partially or fully halogenated, hydroxy, nitrile and $C_{1-3}$ alkoxy which is optionally partially or fully halogenated;
cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; oxo;
$C_{2-4}$ alkynyl optionally partially or fully halogenated wherein one or more methylene groups are optionally replaced by O, and optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms; and each $R_2$ is independently:
a $C_{1-4}$ alkyl optionally partially or fully halogenated, $C_{1-4}$ alkoxy optionally partially or fully halogenated, bromo, chloro, fluoro, methoxycarbonyl, methyl-S(O)$_m$, ethyl-S(O)$_m$ each optionally partially or fully halogenated or phenyl-S(O)$_m$;
or $R_2$ is mono- or di-$C_{1-3}$acylamino, amino-S(O)$_m$ or S(O)$_m$amino wherein the N atom is mono- or di-substituted by $C_{1-3}$alkyl or phenyl, nitrile, nitro or amino.

12. The compound according to claim 11 wherein:
G is:

phenyl, pyridinyl, pyridonyl, 2-naphthyl, quinolinyl, isoquinolinyl, dihydrobenzofuranyl, indanyl, 5-indolyl, indolinyl, indolonyl, or indolinonyl, wherein G is substituted by one $R_3$ and further substituted by one or more $R_1$ or $R_2$;

Ar is 1-naphthyl;

X is:
phenyl, imidazolyl, pyridinyl, pyrimidinyl, piperidinyl, piperazinyl, pyridazinyl or pyrazinyl and wherein X is attached to the 4-position of Ar;

Y is:
a bond or
—$CH_2$—, —$CH_2CH_2$—, O—$CH_2CH_2$—, >C(O), —O—, —S—, —NH—$CH_2CH_2$—, —N($CH_3$)—, $CH_2$(CN)$CH_2$—NH—$CH_2$ or —NH—;

Z is:
morpholinyl optionally substituted by $C_{1-2}$ alkyl or $C_{1-2}$ alkoxy;

$R_1$ is:
$C_{1-5}$ alkyl optionally partially or fully halogenated wherein one or more C atoms are optionally independently replaced by O or N, and wherein said $C_{1-5}$ alkyl is optionally substituted with oxo, dioxolanyl, pyrrolidinyl, furyl or phenyl optionally substituted by $C_{1-3}$ alkoxy;
cyclopropyl, cyclopentanyl, cyclohexanyl and bicyclopentanyl optionally substituted with one to three methyl groups optionally partially or fully halogenated, nitrile, hydroxymethyl or phenyl; or 2-tetrahydrofuranyl substituted by methyl;
propynyl substituted hydroxy or tetrahydropyran-2-yloxy;

$R_2$ is:
is $C_{1-4}$ alkoxy optionally partially or fully halogenated, mono- or di-$C_{1-3}$acylamino, amino-S(O)$_m$ or S(O)$_m$ amino wherein the N atom is mono- or di-substituted by $C_{1-3}$alkyl or phenyl, bromo, chloro, fluoro, nitrile, nitro, amino, methylsulfonyl optionally partially or fully halogenated or phenylsulfonyl; and
$R_a$ is $C_{1-4}$ alkyl optionally substituted by $C_{1-3}$ alkoxy, mono- or di-$C_{1-3}$ alkylamino, mono- or di-$C_{1-3}$ alkylaminocarbonyl; or $R_a$ is heterocycle$C_{0-3}$ alkyl wherein the heterocycle is chosen from morpholinyl, tetrahydrofuranyl, pyrrolidinyl, 2,5-dioxopyrrolidinyl, piperidinyl, 2-oxo-piperidinyl and 3-oxo-morpholinyl, heteroaryl$C_{0-3}$ alkyl wherein the $C_{0-3}$ alkyl portion is optionally substituted by oxo and the heteroaryl is chosen from pyridinyl, imidazolyl, pyrazolyl, thiazolyl and oxazolyl or $R_a$ is $C_{3-6}$ cycloalkyl$C_{0-3}$ alkyl.

13. The compound according to claim 12 wherein:

G is:
phenyl or pyridinyl, wherein G is substituted by one $R_3$ and further substituted by one or more $R_1$ or $R_2$;

X is:
phenyl, imidazolyl, pyridinyl, pyrimidinyl or pyrazinyl;

Y is:
a bond, —$OCH_2CH_2$—, —$CH_2CH_2$—, —O—, $CH_2$(CN)$CH_2$—NH—$CH_2$—, —$CH_2$—, >C(O), —NH—$CH_2CH_2$— or —NH—;

Z is:
morpholinyl, optionally substituted by $C_{1-2}$ alkyl or $C_{1-2}$ alkoxy;

$R_1$ is:

tert-butyl, sec-butyl, tert-amyl, phenyl, tetrahydropyran-2-yloxypropynyl, hydroxypropynyl, trihalomethyl, 2,2-diethylpropionyl or cyclohexanyl;

$R_2$ is:
$C_{1-4}$ alkoxy optionally partially or fully halogenated, chloro, nitro, amino, nitrile, methylsulfonylamino, diacetylamino, phenylsulfonylamino, N,N -di (methylsulfonyl)amino, methylsulfonyl or trihalomethylsulfonyl; and
$R_a$ is $C_{1-4}$ alkyl optionally substituted by $C_{1-3}$ alkoxy, mono- or di-$C_{1-3}$ alkylamino, mono- or di-$C_{1-3}$ alkylaminocarbonyl; or $R_a$ is heterocycleC0–2 alkyl wherein the heterocycle is chosen from morpholinyl, tetrahydrofuranyl, pyrrolidinyl, 2,5-dioxopyrrolidinyl, piperidinyl, 2-oxo-piperidinyl and 3-oxo-morpholinyl, heteroarylC0–2 alkyl wherein the heteroaryl is chosen from piperidinyl and oxazolyl or $R_a$ is $C_{3-6}$ cycloalkyl $C_{0-2}$ alkyl.

14. The compound according to claim 13 wherein:

G is phenyl substituted by $R_3$ and one to two $R_1$ or $R_2$;

X is phenyl, pyridinyl, pyrimidinyl or pyrazinyl;

$R_a$ is $C_{1-4}$ alkyl optionally substituted by $C_{1-3}$ alkoxy, mono- or di-$C_{1-3}$ alkylamino, mono- or di-$C_{1-3}$ alkylaminocarbonyl; or $R_a$ is heterocycle$C_{0-2}$ alkyl wherein the heterocycle is chosen from morpholin-4-yl, tetrahydrofuran-2-yl, pyrrolidin-1 or 2-yl, 2,5-dioxopyrrolidin-1-yl, piperidin-2-yl, 2-oxo-piperidin-3-yl and 3-oxo-morpholin-4-yl, heteroaryl$C_{0-2}$ alkyl wherein the heteroaryl is chosen from piperidin-3 or 4-yl and oxazol-5-yl or $R_a$ is cyclopropylmethyl;

Y is:
—O—, —$CH_2$— or >C(O); and

Z is
morpholin-4-yl optionally substituted by $C_{1-2}$ alkyl.

15. The compound according to claim 14 wherein:

the attachment of X to Ar and Y is at the following X positions: 3,6 pyridinyl, 1,4 phenyl, 2,5 pyrimidinyl and 2,5 pyrazinyl, respectively;

Y is —$CH_2$— or >C(O).

16. A compound wherein the compound is

N-(5-tert-Butyl-2-methoxy-3-{3-[4-(6-morpholin-4-ylmethyl-pyridin-3-yl)-naphthalen-1-yl]-ureido}-phenyl)-2-morpholin-4-yl-2-oxo-acetamide or the pharmaceutically acceptable salts, acids, esters or isomers thereof.

17. A compound chosen from

N-(5-tert-Butyl-2-methoxy-3-{3-[4-(6-morpholin-4-ylmethyl-pyridin-3-yl)-naphthalen-1-yl]-ureido}-phenyl)-N',N'-diethyl-oxalamide;

N-(5-tert-Butyl-2-methoxy-3-{3-[4-(4-morpholin-4-ylmethyl-phenyl)-naphthalen-1-yl]-ureido}-phenyl)-N'-methyl-oxalamide;

N-(5-tert-Butyl-2-methoxy-3-{3-[4-(6-morpholin-4-ylmethyl-pyridin-3-yl)-naphthalen-1-yl]-ureido}-phenyl)-N'-ethyl-oxalamide;

N-(5-tert-Butyl-2-methoxy-3-{3-[4-(6-morpholin-4-ylmethyl-pyridin-3-yl)-naphthalen-1-yl]-ureido}-phenyl)-N',N'-dimethyl-oxalamide;

N-(5-tert-Butyl-2-methoxy-3-{3-[4-(6-morpholin-4-ylmethyl-pyridin-3-yl)-naphthalen-1-yl]-ureido}-phenyl)-2-oxo-2-pyrrolidin-1-yl-acetamide;

N-(5-tert-Butyl-2-methoxy-3-{3-[4-(6-morpholin-4-ylmethyl-pyridin-3-yl)-naphthalen-1-yl]-ureido}-phenyl)-2-oxo-2-piperidin-1-yl-acetamide;

N-(5-tert-Butyl-2-methoxy-3-{3-[4-(6-morpholin-4-ylmethyl-pyridin-3-yl)-naphthalen-1-yl]-ureido}-phenyl)-2-oxo-2-piperazin-1-yl-acetamide and N-(5-tert-Butyl-2-methoxy-3-{3-[4-(4-morpholin-4-ylmethyl-phenyl)-naphthalen-1-yl]-ureido}-phenyl)-2-oxo-2-piperazin-1-yl-acetamide or the pharmaceutically acceptable salts, acids, esters or isomers thereof.

18. A compound chosen from (5-tert-Butyl-2-methoxy-3-{3-[4-(6-morpholin-4-ylmethyl-pyridin-3-yl)-naphthalen-1yl]-ureido}-phenyl)-carbamic acid methyl ester;

(5-tert-Butyl-2-methoxy-3-{3-[4-(6-morpholin-4-ylmethyl-pyridin-3-yl)-naphthalen-1yl]-ureido}-phenyl)-carbamic acid isopropyl ester;

(5-tert-Butyl-2-methoxy-3-{3-[4-(6-morpholin-4-ylmethyl-pyridin-3-yl)-naphthalen-1yl]-ureido}-phenyl)-carbamic acid 2-methoxy-ethyl ester;

(5-tert-Butyl-2-methoxy-3-{3-[4-(6-morpholin-4-ylmethyl-pyridin-3-yl)-naphthalen-1yl]-ureido}-phenyl)-carbamic acid ethyl ester and (5-tert-Butyl-2-methoxy-3-{3-[4-(6-morpholin-4-ylmethyl-pyridin-3-yl)-naphthalen-1-yl]-ureido}-phenyl)-carbamic acid 2-morpholin-4-yl-ethyl ester or the pharmaceutically acceptable salts, acids, esters or isomers thereof.

19. A compound chosen from (5-tert-Butyl-2-methoxy-3-{3-[4-(2-morpholin-4-ylmethyl-pyrimidin-5-yl)-naphthalen-1-yl]-ureido}-phenyl)-carbamic acid cyclopropylmethyl ester;

(5-tert-Butyl-2-methoxy-3-{3-[4-(6-morpholin-4-ylmethyl-pyridin-3-yl)-naphthalen-1yl]-ureido}-phenyl)-carbamic acid tert-butyl ester;

(5-tert-Butyl-2-methoxy-3-{3-[4-(2-morpholin-4-ylmethyl-pyrimidin-5-yl)-naphthalen-1-yl]-ureido}-phenyl)-carbamic acid tetrahydro-furan-2-ylmethyl ester;

(5-tert-Butyl-2-methoxy-3-{3-[4-(6-morpholin-4-ylmethyl-pyridin-3-yl)-naphthalen-1yl]-ureido}-phenyl)-carbamic acid tetrahydro-furan-2-ylmethyl ester;

(5-tert-Butyl-2-methoxy-3-{3-[4-(6-morpholin-4-ylmethyl-pyridin-3-yl)-naphthalen-1yl]-ureido}-phenyl)-carbamic acid 1-methyl-pyrrolidin-2-ylmethyl ester;

(5-tert-Butyl-2-methoxy-3-{3-[4-(4-morpholin-4-ylmethyl-phenyl)-naphthalen-1-yl]-ureido}-phenyl)-carbamic acid 1-methyl-pyrrolidin-2-ylmethyl ester;

(5-tert-Butyl-2-methoxy-3-{3-[4-(4-morpholin-4-ylmethyl-phenyl)-naphthalen-1-yl]-ureido}-phenyl)-carbamic acid 2-pyrrolidin-1-yl-ethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid 2-dimethylamino-ethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid 2-(2,5-dioxo-pyrrolidin-1-yl)-ethyl ester;

[5-tert-Butyl-2-methoxy-3-(3-{4-[2-(morpholine-4-carbonyl)-pyrimidin-5-yl]-naphthalen-1-yl}-ureido)-phenyl]-carbamic acid 2-dimethylamino-propyl ester;

[5-tert-Butyl-2-methoxy-3-(3-{4-[5-(morpholine-4-carbonyl)-pyrazin-2-yl]-naphthalen-1-yl}-ureido)-phenyl]-carbamic acid 2-dimethylamino-propyl ester;

(5-tert-Butyl-2-methoxy-3-{3-[4-(6-morpholin-4-ylmethyl-pyridin-3-yl)-naphthalen-1-yl]-ureido}-phenyl)-carbamic acid 2-dimethylamino-2-methyl-propyl ester;

[5-tert-Butyl-2-methoxy-3-(3-{4-[6-(morpholine-4-carbonyl)-pyridin-3-yl]-naphthalen-1-yl}-ureido)-phenyl]-carbamic acid 1-methyl-piperidin-2-ylmethyl ester;

[5-tert-Butyl-2-methoxy-3-(3-{4-[6-(morpholine-4-carbonyl)-pyridin-3-yl]-naphthalen-1-yl }-ureido)-phenyl]-carbamic acid dimethylcarbamoylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid methylcarbamoylmethyl ester;

(5-tert-Butyl-2-methoxy-3-{3-[4-(2-morpholin-4-ylmethyl-pyrimidin-5-yl)-naphthalen-1-yl]-ureido}-phenyl)-carbamic acid methylcarbamoylmethyl ester;

[5-tert-Butyl-2-methoxy-3-(3-{4-[2-(morpholine-4-carbonyl)-pyrimidin-5-yl]-naphthalen-1-yl}-ureido)-phenyl]-carbamic acid carbamoylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid carbamoylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid 2-oxo-2-pyrrolidin-1-yl-ethyl ester;

(5-tert-Butyl-2-methoxy-3-{3-[4-(5-morpholin-4-ylmethyl-pyrazin-2-yl)-naphthalen-1-yl]-ureido}-phenyl)-carbamic acid 2-oxo-piperidin-3-yl ester;

(5-tert-Butyl-2-methoxy-3-{3-[4-(5-morpholin-4-ylmethyl-pyrazin-2-yl)-naphthalen-1-yl]-ureido}-phenyl)-carbamic acid pyridin-3-ylmethyl ester;

[5-tert-Butyl-2-methoxy-3-(3-{4-[5-(morpholine-4-carbonyl)-pyrazin-2-yl]-naphthalen-1-yl}-ureido)-phenyl]-carbamic acid oxazol-5-ylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid oxazol-5-ylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid pyridin-4-ylmethyl ester;

(5-tert-Butyl-2-methoxy-3-{3-[4-(6-morpholin-4-ylmethyl-pyridin-3-yl)-naphthalen-1-yl]-ureido}-phenyl)-carbamic acid 2-(3-oxo-morpholin-4-yl)-ethyl ester; and or the pharmaceutically acceptable derivatives thereof.

20. A pharmaceutical composition comprising a pharmaceutically effective amount of a compound according to claim 1.

21. A method of treating a disease or condition selected from rheumatoid arthritis, inflammatory bowel disease, osteoarthritis, Crohn's disease, ulcerative colitis, Guillain-Barre syndrome, psoriasis, graft versus host disease, systemic lupus erythematosus, percutaneous transluminal coronary angioplasty, toxic shock syndrome, acute and chronic pain, contact dermatitis, atherosclerosis, traumatic arthritis, glomerulonephritis, reperfusion injury, bone resorption disease, chronic obstructive pulmonary disease, asthma, myocardial infarction, thermal injury, adult respiratory distress syndrome (ARDS), multiple organ injury secondary to trauma, dermatoses with acute inflammatory components, acute purulent meningitis, necrotizing entrerocolitis, syndromes associated with hermodialysis, leukopherisis and granulocyte transfusion comprising administering to a patient a threapeutically effective amount of a compound according to a claim 1.

22. The method according to claim 21 wherein the disease is selected from rheumatoid arthritis, osteoarthritis, Crohn's disease, psoriasis, ulcerative colitis, osteoporosis and chronic obstructive pulmonary disease.

23. The method according to claim 22 wherein the disease is selected from rheumatoid arthritis, Crohn's disease, psoriasis and chronic obstructive pulmonary disease.

24. A method of making a compound of the formula(I) according to claim 1, comprising:
   a) reacting an arylamine with 2,2,2-trichloroethylchloroformate in a suitable halogenated solvent with a suitable base at 0–85° C. for about 2–24 hours:

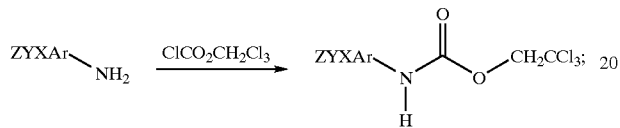

b) isolating and subsequently reacting the product of step a) with an arylamine shown below in a non-protic anhydrous solvent at 0–110° C. for about 2–24 hours, to produce a compound of the formula (I):

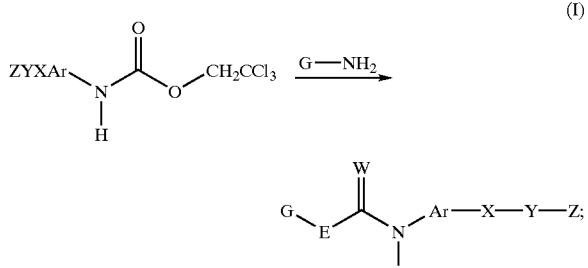

wherein E is N—H, W is O and G, Ar, X, Y and Z are as defined in claim 1.

* * * * *